United States Patent
Huang et al.

(10) Patent No.: US 10,786,551 B2
(45) Date of Patent: Sep. 29, 2020

(54) USE OF INTERLEUKIN-22 IN THE TREATMENT OF FATTY LIVER DISEASE

(71) Applicant: Generon (Shanghai) Corporation Ltd., Shanghai (CN)

(72) Inventors: Yu Liang Huang, Shanghai (CN); Zhi Hua Huang, Shanghai (CN); Qi Sun, Shanghai (CN)

(73) Assignee: Generon (Shanghai) Corporation Ltd., Shanghai (CN)

(*) Notice: Subject to any disclaimer, the term of this patent is extended or adjusted under 35 U.S.C. 154(b) by 0 days.

(21) Appl. No.: 15/694,670

(22) Filed: Sep. 1, 2017

(65) Prior Publication Data

US 2018/0028614 A1    Feb. 1, 2018

Related U.S. Application Data

(60) Continuation of application No. 14/483,175, filed on Sep. 11, 2014, now abandoned, which is a division of application No. 12/672,274, filed as application No. PCT/US2008/071859 on Aug. 1, 2008, now abandoned.

(30) Foreign Application Priority Data

Aug. 6, 2007  (CN) .......................... 2007 1 0044592

(51) Int. Cl.
  *A61K 38/20*    (2006.01)

(52) U.S. Cl.
  CPC .................................. *A61K 38/20* (2013.01)

(58) Field of Classification Search
  None
  See application file for complete search history.

(56) References Cited

U.S. PATENT DOCUMENTS

| | | |
|---|---|---|
| 4,179,337 A | 12/1979 | Davis et al. |
| 4,301,144 A | 11/1981 | Iwashita et al. |
| 4,399,216 A | 8/1983 | Axel et al. |
| 4,496,689 A | 1/1985 | Mitra |
| 4,640,835 A | 2/1987 | Shimizu et al. |
| 4,657,760 A | 4/1987 | Kung et al. |
| 4,670,417 A | 6/1987 | Iwasaki et al. |
| 4,683,195 A | 7/1987 | Mullis et al. |
| 4,683,202 A | 7/1987 | Mullis |
| 4,791,192 A | 12/1988 | Nakagawa et al. |
| 4,849,227 A | 7/1989 | Cho |
| 4,943,529 A | 7/1990 | Van den Berg et al. |
| 4,965,188 A | 10/1990 | Mullis et al. |
| 5,010,182 A | 4/1991 | Brake et al. |
| 5,206,344 A | 4/1993 | Katre et al. |
| 5,225,212 A | 7/1993 | Martin et al. |
| 5,428,130 A | 6/1995 | Capon et al. |
| 5,654,010 A | 8/1997 | Johnson et al. |
| 6,274,710 B1 | 8/2001 | Dumoutier et al. |
| 6,331,613 B1 | 12/2001 | Dumoutier et al. |
| 6,359,117 B1 | 3/2002 | Dumoutier et al. |
| 6,551,799 B2 | 4/2003 | Gurney et al. |
| 6,797,493 B2 | 9/2004 | Sun et al. |
| 7,226,591 B2 | 6/2007 | Gurney et al. |
| 7,307,161 B1 | 12/2007 | Jacobs et al. |
| 7,459,533 B2 | 12/2008 | Jacobs et al. |
| 7,585,646 B2 | 9/2009 | Jacobs et al. |
| 7,651,694 B2 | 1/2010 | Lee |
| 7,666,402 B2* | 2/2010 | Huang .................. A61K 38/20 424/85.2 |
| 7,696,158 B2* | 4/2010 | Huang .................. A61K 38/20 424/85.2 |
| 7,718,604 B2* | 5/2010 | Huang .................. A61K 38/20 424/85.2 |
| 7,972,833 B2 | 7/2011 | Dumoutier et al. |
| 8,048,984 B2 | 11/2011 | Jacobs et al. |
| 8,178,082 B2 | 5/2012 | Gurney et al. |
| 8,178,675 B2* | 5/2012 | Romantsev .......... A61K 31/216 546/1 |
| 8,945,528 B2 | 2/2015 | Yan et al. |
| 8,956,605 B2 | 2/2015 | Huang et al. |
| 9,352,024 B2 | 5/2016 | Wu et al. |
| 9,629,898 B2 | 4/2017 | Yan et al. |
| 10,087,227 B2 | 10/2018 | Scheer et al. |
| 10,160,793 B2 | 12/2018 | Scheer et al. |
| 10,543,169 B2 | 1/2020 | Yan et al. |
| 2001/0023070 A1 | 9/2001 | Ebner et al. |
| 2002/0102723 A1 | 8/2002 | Gurney et al. |
| 2003/0100076 A1 | 5/2003 | Gurney et al. |
| 2003/0235561 A1 | 12/2003 | Vandenburgh et al. |
| 2005/0148029 A1 | 7/2005 | Buechler et al. |

(Continued)

FOREIGN PATENT DOCUMENTS

| CA | 2695734 A1 | 2/2009 |
|---|---|---|
| CA | 2705007 A1 | 5/2009 |

(Continued)

OTHER PUBLICATIONS

Radaeva et al.., Hepatology, vol. 39, p. 1332-1342 (Year: 2004).*
Adachi et al., Dig. Dis., vol. 23, pp. 255-263 (Year: 2005).*
Adams et al. Postgrad Med. J, vol. 82, pp. 315-322. (Year: 2006).*
Lieber et al., Gasteroenterology, vol. 50, No. 3, pp. 316-322. (Year: 1966).*
Browning et al., J. Clin. Invest., vol. 114, No. 2, pp. 147-152 (Year: 2004).*
Mavrelis et al., Hepatology, vol. 3, No. 2, pp. 226-231. (Year: 1983).*

(Continued)

*Primary Examiner* — Daniel E Kolker
*Assistant Examiner* — Jegatheesan Seharaseyon
(74) *Attorney, Agent, or Firm* — Morrison & Foerster LLP

(57) ABSTRACT

The present invention relates to use of interleukin-22 (IL-22) for treating fatty liver disease by decreasing the levels of transaminases. The use of IL-22 in decreasing the levels of transaminases is also provided.

12 Claims, 12 Drawing Sheets
Specification includes a Sequence Listing.

(56) References Cited

U.S. PATENT DOCUMENTS

| | | |
|---|---|---|
| 2007/0172457 A1 | 7/2007 | Ebner et al. |
| 2007/0207943 A1 | 9/2007 | Ebner et al. |
| 2008/0031882 A1 | 2/2008 | Liang et al. |
| 2008/0069798 A1 | 3/2008 | Huang et al. |
| 2008/0069799 A1 | 3/2008 | Huang et al. |
| 2008/0138314 A1 | 6/2008 | Huang et al. |
| 2008/0241246 A1 | 10/2008 | Sakthivel et al. |
| 2008/0293629 A1 | 11/2008 | Rosen et al. |
| 2009/0202475 A1 | 8/2009 | Abbas et al. |
| 2009/0221008 A1 | 9/2009 | Yu et al. |
| 2010/0015086 A1 | 1/2010 | Huang et al. |
| 2011/0091417 A1 | 4/2011 | Gurney et al. |
| 2011/0262385 A1 | 10/2011 | Huang et al. |
| 2011/0268696 A1 | 11/2011 | Huang et al. |
| 2011/0280828 A1 | 11/2011 | Abbas et al. |
| 2013/0171100 A1 | 7/2013 | Yan et al. |
| 2014/0314711 A1 | 10/2014 | Scheer et al. |
| 2014/0377222 A1 | 12/2014 | Huang et al. |
| 2015/0147293 A1 | 5/2015 | Wu et al. |
| 2015/0202267 A1 | 6/2015 | Yan et al. |
| 2016/0263020 A1 | 9/2016 | Yan et al. |
| 2016/0271221 A1 | 9/2016 | Yan et al. |
| 2016/0287670 A1 | 10/2016 | Brink et al. |
| 2017/0088596 A1 | 3/2017 | Scheer et al. |
| 2017/0320926 A1 | 11/2017 | Scheer et al. |

FOREIGN PATENT DOCUMENTS

| | | | |
|---|---|---|---|
| CN | 1264596 A | | 8/2000 |
| CN | 1381512 A | | 11/2002 |
| CN | 101168049 A | * | 4/2008 |
| CN | 101218254 A | | 7/2008 |
| CN | 101225110 A | | 7/2008 |
| CN | 102380091 A | | 3/2012 |
| CN | 103118699 A | | 5/2013 |
| EP | 0 036 776 A2 | | 9/1981 |
| EP | 0 073 657 A1 | | 3/1983 |
| EP | 0 117 058 A2 | | 8/1984 |
| EP | 0 117 060 A2 | | 8/1984 |
| EP | 0 139 383 A1 | | 5/1985 |
| EP | 0 183 070 A2 | | 6/1986 |
| EP | 0 244 234 A2 | | 11/1987 |
| EP | 0 362 179 A2 | | 4/1990 |
| EP | 0 394 538 A1 | | 10/1990 |
| EP | 0 402 226 A1 | | 12/1990 |
| EP | 1748789 B1 | | 12/2010 |
| JP | 2008-508862 A | | 3/2008 |
| JP | 2011507863 A | | 3/2011 |
| JP | 2013-536254 A | | 9/2013 |
| WO | WO-1997/03692 A1 | | 2/1977 |
| WO | WO-1987/05330 A1 | | 9/1987 |
| WO | WO-1989/05859 A1 | | 6/1989 |
| WO | WO-1991/00357 A1 | | 1/1991 |
| WO | WO-1995/013312 A1 | | 5/1995 |
| WO | WO-1995/022419 A1 | | 8/1995 |
| WO | WO-1996/07399 A1 | | 3/1996 |
| WO | WO-1996/40072 A2 | | 12/1996 |
| WO | WO-1999/32139 A1 | | 7/1999 |
| WO | WO-1999/61617 A1 | | 12/1999 |
| WO | WO-2002/029098 A2 | | 4/2002 |
| WO | WO-2003/013589 A1 | | 2/2003 |
| WO | WO-2003/089569 A2 | | 10/2003 |
| WO | WO-2005/044292 A2 | | 5/2005 |
| WO | WO-2006/000448 A2 | | 1/2006 |
| WO | WO-2006/000448 A3 | | 1/2006 |
| WO | WO-2006073508 A1 | * | 7/2006 ............. A61K 38/20 |
| WO | WO-2006/088833 A2 | | 8/2006 |
| WO | WO-2006/088833 A3 | | 8/2006 |
| WO | WO-2007/047796 A2 | | 4/2007 |
| WO | WO-2007/115230 A2 | | 10/2007 |
| WO | WO-2007/115230 A3 | | 10/2007 |
| WO | WO-2009/020844 A1 | | 2/2009 |
| WO | WO-2009/041734 A1 | | 4/2009 |
| WO | WO-2009/062102 A2 | | 5/2009 |
| WO | WO-2009/062102 A3 | | 5/2009 |
| WO | WO2009079024 A1 | | 6/2009 |
| WO | WO-2010/081112 A1 | | 7/2010 |
| WO | WO-2011/087986 A1 | | 7/2011 |
| WO | WO-2012/028089 A1 | | 3/2012 |
| WO | WO-2013/097748 A1 | | 7/2013 |
| WO | WO-2014/145016 A2 | | 9/2014 |
| WO | WO-2015/067198 A1 | | 5/2015 |
| WO | WO-2015/067199 A1 | | 5/2015 |
| WO | WO-2015/070077 A1 | | 5/2015 |
| WO | WO-2017/181143 A1 | | 10/2017 |

OTHER PUBLICATIONS

Yamaguchi et al. (Hepatology, vol. 45, pp. 1366-1374) (Year: 2007).*

Caballero et al. (Journal of Hepatology,vol. 50, pp. 789-796) (Year: 2009).*

Xu et al. CN101168049A pp. 1-18 (English translation from Espacenet (Year: 2008).*

Asiedu, C. et al. (2007). "Cloning and Characterization of Recombinant Rhesus Macaque IL-10/Fc($^{ala-ala}$) Fusion Protein: A Potential Adjunct for Tolerance Induction Strategies," *Cytokine* 40:183-192.

Aujla, S.J. et al. (Mar. 2008, e-pub. Feb. 10, 2008). "IL-22 Mediates Mucosal Host Defense Against Gram-Negative Bacterial Pneumonia," *Nat Med* 14:275-281.

Ballance, D.J. et al. (Apr. 15, 1983). "Transformation of Aspergillus Nidulans by the Orotidine- 5'-Phosphate Decarboxylase Gene of *Neurospora crassa*," *Biochem. Biophys. Res. Commum.* 112(1):284-289.

Balthazar, E.J. et al. (Feb. 1990). "Acute Pancreatitis: Value of CT in Establishing Prognosis," *Radiology* 174(2):331-336.

Balthazar, E.J. et al. (Sep. 1985). "Acute Pancreatitis: Prognostic Value of CT," *Radiology* 156(3):767-772.

Banks, P.A. et al. (Oct. 2006). "Practice Guidelines in Acute Pancreatitis," *The American Journal of Gastroenterology* 101(10): 2379-2400.

Barker, N. et al. (Oct. 25, 2007, e-pub. Oct. 14, 2007). "Identification of Stem Cells in Small Intestine and Colon by Marker Gene LGR5," *Nature* 449:1003-1007.

Beach, D. et al. (Mar. 12, 1981). "High-frequency Transformation of the Fission Yeast *Schizosaccharomyces pombe*," *Nature* 290:140-142.

Case, M. E. et al. (Oct. 1979)."Efficient transformation of *Neurospora. crassa* Utilizing Hybrid Plasmid DNA," *Proc. Natl. Acad. Sci. U. S. A.* 76(10):5259-5263.

Chan, H.L-Y. et al. (Jun. 2007). "How Should We Manage Patients With Non-Alcoholic Fatty Liver Disease In 2007?" *Journal of Gastroenterology and Hepatology* 22(6):801-808.

Chang, A.C.Y. et al. (Oct. 19, 1978). "Phenotypic Expression in *E. coli* of a DNA Sequence Coding for Mouse Dihydrofolate Reductase," *Nature* 275(5681):617-624.

Clayburgh, D.R. et al. (Mar. 2004; e-published on Jan. 19, 2004). "A Porous Defense: the Leaky Epithelial Barrier in Intestinal Disease," *Lab Invest* 84(3):282-291.

Cox, G.N. et al. (2004). "Enhanced Circulating Half-Life and Hematopoietic Properties of a Human Granulocyte Colony-Stimulating Factor/Immunoglobulin Fusion Protein," *Exp. Hematol.* 32:441-449.

Dambacher, J. et al. (Mar. 2008). "The Role of Interleukin-22 in Hepatitis C Virus Infection," *Cytokine* 41(3):209-216.

De Boer et al. (Jan. 1983). "The tac Promotor: A Functional Hybrid Derived from the trp and lac Promotors," *Proc. Natl. Acad. Sci. USA* 80:21-25.

De Oliveira Neto, M. et al. (Mar. 1, 2008; e-pub. Nov. 16, 2007). "Interleukin-22 Forms Dimers That are Recognized by Two Interleukin-22R1 Receptor Chains," *Biophys. J.* 94(5):1754-1765.

Dimartino, J.F. et al. (Sep. 1999). "Ml1 Rearrangements in Haematological Malignancies: Lessons from Clinical and Biological Studies," *Br J Haematol.* 106(3):614-626.

Dumoutier, L. et al. (Aug. 29, 2000). "Human Interleukin-10-Related T Cell-Derived Inducible Factor: Molecular Cloning and Functional Characterization as an Hepatocyte-Stimulating Factor," *PNAS* 97(18):10144-10149.

(56) References Cited

OTHER PUBLICATIONS

Dumoutier, L. et al. (Feb. 15, 2000). "Cloning and Characterization of IL-10-Related T Cell-Derived Inducible Factor (IL-TIF), a Novel Cytokine Structurally Related to IL-10 and Inducible by IL-9[1]," *The Journal of Immunology* 164(4):1814-1819.
Fleer, R. et al. (Oct. 1, 1991). "Stable Multicopy Vectors for High-Level Secretion of Recombinant Human Serum Albumin by Kluyveromyces Yeasts," *Bio/Technology* 9(10):968-975.
Gao, B. (Apr. 2005). "Cytokines, STATs and Liver Disease," *Cell. Mol. Immunol.* 2(2):92-100.
Gao, H. et al. (Jun. 2006). "Long-Term Administration of Estradiol Decreases Expression of Hepatic Lipogenic Genes and Improves Insulin Sensitivity in ob/ob Mice: A Possible Mechanism Is through Direct Regulation of Signal Transducer and Activator of Transcription 3," *Molecular Endocrinology* 20(6):1287-1299.
Gerbitz, A. et al. (Jun. 1, 2004, e-pub. Feb. 12, 2004). "Probiotic Effects on Experimental Graft-Versus-Host Disease: Let Them Eat Yogurt," *Blood* 103(11):4365-4367.
Gething, M.J. et al. (Oct. 22, 1981) "Cell-Surface Expression of Influenza Haemagglutinin from a Cloned DNA Copy of the RNA Gene," *Nature*, 293:620-625.
Gill, H.K. et al. (Jan. 21, 2006). "Non-Alcoholic Fatty Liver Disease and the Metabolic Syndrome: Effects of Weight Loss and a Review of Popular Diets. Are Low Carbohydrate Diets the Answer?" *World Journal of Gastroenterology* 12(3):345-353.
Goeddel, D.V. et al. (Oct. 18, 1979). "Direct Expression in *Escherichia coli* of a DNA Sequence Coding For Human Growth Hormone," *Nature* 281:544-548.
Goeddel, D.V. et al. (Sep. 25, 1980). "Synthesis of Human Fibroblast Interferon by *E. coli*," *Nucleic Acids Res.* 8(18):4057-4074.
Graham, F.L. et al. (1977). "Characteristics of a Human Cell Line Transformed by DNA from Human Adenovirus Type 5," *J. Gen Virol*, 36:59-72.
Graham, F.L. et al. (Apr. 1973). "A New Technique for the Assay of Infectivity of Human Adenovirus 5 DNA," *Virology* 52(2):456-467.
Grattagliano, I. et al. (May 2007). "Managing Nonalcoholic Fatty Liver Disease: Recommendations for Family Physicians," *Canadian Family Physician* 53(5):857-863.
Greenwald, R.B. et al. (Oct. 20, 1994). "Highly Water Soluble Taxol Derivatives: 2'-Polyethyleneglycol Esters as Potential Prodrugs," *Bioorg. Med. Chem. Lett.* 4(20):2465-2470.
Henikoff, S. et al. (Nov. 15, 1992). "Amino Acid Substitution Matrices From Protein Blocks," *Proc. Nat'l Acad. Sci. USA* 89:10915-10919.
Hess, B. et al. (1969). "Cooperation of Glycolytic Enzymes," *Adv Enzyme Regul.* 7:149-167.
Hill, G.R. et al. (May 1, 2000). "The Primacy of the Gastrointestinal Tract as a Target Organ of Acute Graft-Versus-Host Disease: Rationale for the use of Cytokine Shields in Allogeneic Bone Marrow Transplantation," *Blood* 95(9):2754-2759.
Hines, I.N. et al. (Aug. 2004). "Recent Advances in Alcoholic Liver Disease III. Role of the Innate Immune Response in Alcoholic Hepatitis," *American Journal of Physiology—Gastrointestinal and Liver Physiology* 287(2):G310-G314.
Hitzeman, R.A. et al. (Dec. 25, 1980). "Isolation and Characterization of the Yeast 3-Phosphoglycerokinase Gene (PKG) by an Immunological Screening Technique," *J. Biol. Chem.* 255(24):12073-12080.
Holland, J.P. (Nov. 14, 1978). "Isolation and Identification of Yeast Messenger Ribonucleic Acids Coding For Enolase, Glyceraldehyde-3-Phosphate Dehydrogenase, and Phosphoglycerate Kinase," *Biochemistry* 17(23):4900-4907.
Hong, F. et al. (Oct. 2004). "Interleukin 6 Alleviates Hepatic Steatosis and Ischemia/Reperfusion Injury in Mice with Fatty Liver Disease," *Hepatology* 40(4):933-941.
Hsiao, C.L. et al. (Aug. 1979). "High-Frequency Transformation of Yeast by Plasmids Containing the Cloned Yeast ARG4 Gene," *Proc. Natl. Acad. Sci. (USA)* 76(8):3829-3833.
International Diabetes Federation. (2006). "The IDF Consensus Worldwide definition of the metabolic Syndrome," 24 pages.

Johnson, O.L. et al. (Jul. 1996). "A Month-Long Effect from a Single Injection of Microencapsulated Human Growth Hormone," *Nature Medicine* 2(7):795-799.
Jones, B.C. et al. (Apr. 1, 2008; e-pub. Mar. 21, 2008). "Crystallization and Preliminary X-Ray Diffraction Analysis of Human IL-22 Bound to the Extracellular IL-22R1 Chain," *Acta Crystall. Sect. F. Structure Biol. Cryst. Commun.* 64(Pt. 4):266-269.
Jones, E.W. (Jan. 1977). "Proteinase Mutants of *Saccharomyces cerevisiae*," *Genetics* 85(1):23-33.
Inoue, H. et al. (Feb. 2004; e-published on Jan. 11, 2004). "Role of STAT-3 in Regulation of Hepatic Gluconeogenic Genes and Carbohydrate Metabolism In Vivo," Nat Med. 10(2):168-174. English Replacement of: Inoue, H. et al. (Feb. 2004; e-published on Jan. 11, 2004). "Role of STAT-3 in Regulation of Hepatic Gluconeogenic Genes and Carbohydrate Metabolism In Vivo," Experimental Medicine 22(7):970-973.
Kelly, J.M. et al. (Feb. 1985). "Transformation of Aspergillus Niger by the amdS Gene of *Aspergillus nidulans*," *EMBO J.* 4(2):475-479.
Keown, W.A. et al. (1990). "Methods for Introducing DNA into Mammalian Cells," *Methods in Enzymology* 185:527-537.
Kingsman, A.J. et al. (Oct. 1979). "Replication in *Saccharomyces cerevisiae* of Plasmid pBR313 Carrying DNA from the Yeast trpl Region," *Gene* 7(2):141-152.
Klöppel, G. et al. (1991). "Chronic Pancreatitis: Evolution of the Disease," *Hepato-gastroenterology* 38(5):408-412.
Kotenko, S.V. et al. (Sep. 8, 1995). "Interaction Between the Components of the Interferon γ Receptor Complex," *J. Biol. Chem.* 270(36):20915-20921.
Kreymborg, K. et al. (Dec. 2007). "IL-22 is Expressed by Th17 Cells in an IL-23—Dependent Fashion, but Not Required for the Development of Autoimmune Encephalomyelitis," *J Immunol* 179:8098-8104.
Krivtsov, A.V. et al. (Aug. 2006, e-pub. Jul. 16, 2006) "Transformation from Committed Progenitor to Leukaemia Stem Cell Initiated by MLL-AF9," *Nature*. 442(7104):818-822.
Lei, K. et al. (May 19, 1995). "Structure-Function Analysis of Human Glucose-6-Phosphatese, the Enzyme Deficient in Glycogen Storage Disease Type 1a*," *The Journal of Biological Chemistry* 270(20):11882-11886.
Lewis, D.H. (1990). "Controlled Release of Bioactive Agents From Lactide/Glycolide Polymer," in Chapter 1 of *Biodegradable Polymers as Drug Delivery Systems*, Chasin, M. (ed.) et al., Marcel Dekker Inc. New York, 1990, pp. 1-41, fifty two pages.
Li, Q. (Sep. 2003). "Research Development of Interleukin-22," *Chinese J. of Cancer Biotherapy* 10(3):226-228 (Translation of Abstract Only).
Louvencourt, L.D. et al. (May 1983). "Transformation of *Kluyveromyces lactis* by Killer Plasmid DNA," *J. Bacterial.* 154(2):737-742.
Low, S.C. et al. (Jul. 2005). "Oral and pulmonary delivery of FSH-Fc fusion proteins via neonatal Fc receptor-mediated transcytosis," *Human Reproduction* 20(7):1805-1813.
Mansour, S.L. et al. (Nov. 24, 1988). "Disruption of the Proto-Oncogene Int-2 in Mouse Embryo-Derived Stem Cells: A General Strategy For Targeting Mutations to Non-Selectable Genes," *Nature* 336:348-352.
Mantei, N. et al. (Sep. 6, 1979) "Rabbit β-globin mRNA Production in Mouse Cells Transformed with Cloned Rabbit β-Globin Chromosomal DNA," *Nature* 281:40-46.
Marchesini, G. et al. (Aug. 2001). "Nonalcoholic Fatty Liver Disease," *Diabetes* 50(8):1844-1850.
Mather, J.P. (Aug. 1980) "Establishment and Characterization of Two Distinct Mouse Testicular Epithelial Cell Lines," *Biol. Reprod.* 23(1):243-252.
Matsusue, K. et al. (Mar. 2003). "Liver-Specific Disruption Of Pparγ In Lepiin-Deficient Mice Improves Fatty Liver But Aggravates Diabetic Phenotyps," *J. Clin. Invest.* 111(5):737-747.
Max Bayard, M.D. et al. (Jun. 1, 2006). "Nonalcoholic Fatty Liver Disease," *American Family Physician* 73(11):1961-1968.
Mordenti, J. et al. (1989). "The Use of Interspecies Scaling in Toxicokinetics," Chapter 4 in *Toxicokinetics and New Drug Development*, Yacobi A. ed. et al.; Pergamon Press, New York, pp. 42-96.

(56) References Cited

OTHER PUBLICATIONS

Mortele, K.J. et al. (Nov. 2004). "A Modified CT Severity Index for Evaluating Acute Pancreatitis: Improved Correlation With Patient Outcome," *American Journal of Roentgenology* 183:1261-1265.

Nagalakshmi, M.L. et al. (May 2004) "Interleukin-22 Activates STAT3 and Induces IL-10 by Colon Epithelial Cells," *International Immunopharmacology* 4(5):679-691.

Pan, H. et al. (Feb. 2004). "Hydrodynamic Gene Delivery of Interleukin-22 Protects the Mouse Liver from Concanavalin A-, Carbon Tetrachloride-, and Fas Ligand-Induced Injury Via Activation of STAT3," *Cell. Mol. Immunol.* 1(1):43-49.

Riley, P. et al. (Dec. 2007; e-published on May 4, 2007). "A Growing Burden: The Pathogenesis, Investigation and Management of Non-Alcoholic Fatty Liver Disease," *Journal of Clinical Pathology* 60(12):1384-1391.

Sale, G.E. (Mar. 1996) "Does Graft-Versus-Host Disease Attack Epithelial Stem Cells?," *Mol Med Today* 2(3):114-119.

Sambrook, J. et al. (1989). *Molecular Cloning—A Laboratory Manual*, $2^{nd}$ Edition, Maniatis, T. (ed.) et al., Cold Spring Harbor Laboratory Press, New York, NY pp. v-xxxii, twenty nine pages, (Table of Contents only).

Schmidt, J. et al. (Jan. 1992). "A Better Model of Acute Pancreatitis for Evaluating Therapy," *Annals of Surgery* 215(1):44-56.

Shaw, C.H. et.al. (Sep. 1983). "A General Method for the Transfer of Cloned Genes to Plant Cells," *Gene* 23(3):315-330.

Shlomchik, E.D. (May 2007) "Graft-Versus-Host Disease," *Nat. Rev. Immunol.* 7(5):340-352.

Sreekrishna, K. et al. (1988). "High Level Expression of Heterologous Proteins in Methylotrophic Yeast *Pichia pastoris*," *J. Basic Microbial.* 28(4):265-278.

Stinchcomb, D.T. et al. (Nov. 1, 1979). "Isolation and Characterisation of a Yeast Chromosomal Replicator," *Nature* 282:39-43.

Stubbs, M.C. et al. (Jan. 2008, e-pub. Sep. 13, 2007). "MLL-AF9 and FLT3 Cooperation in Acute Myelogenous Leukemia: Development of a Model for Rapid Therapeutic Assessment," *Leukemia* 22:66-77.

Sugimoto, K. et al. (Feb. 2008). "IL-22 Ameliorates Intestinal Inflammation in a Mouse Model of Ulcerative Colitis," *The Journal of Clinical Investigation* 118(2): 534-544.

Tilburn, J. et.al. (Dec. 1983). "Transformation by Integration in *Aspergillus nidulans*," *Gene* 26(2-3):205-221.

Tschemper, G. et al. (Jul. 1980). "Sequence of a Yeast DNA Fragment Containing a Chromosomal Replicator and the TRP1 Gene," *Gene* 10(2):157-166.

Tsunoda, S. et al. (May 1995). "Characterization of PEG-IL-6 and its Thrombopoetic Activity in Vivo," *Drug Delivery System* 10(3):175-180; (with English introduction).

Ueki, K. et al. (Jul. 13, 2004). "Central Role of Suppressors 0f Cytokine Signaling Proteins in Hepatic Steatosis, Insulin Resistance, and the Metabolic Syndrome in the Mouse," *PNAS* 101(28):10422-10427.

Urlaub, G. et al. (Jul. 1980). "Isolation of Chinese Hamster Cell Mutants Deficient in Dihydrofolate Reductase Activity," *Proc. Natl. Acad. Sci. USA* 77(7):4216-4220.

Van Den Berg, J.A. et al. (Feb. 1990). "*Kluyveromyces* as a Host For Heterologous Gene Expression: Expression and Secretion of Prochymosin," *Bio/Technology* 8(2):135-139.

Van Solingen, P. et al. (May 1977). "Fusion of Yeast Spheroplasts," *Journal of Bacteriology* 130(2):946-947.

Wolk, K. et al. (Jun. 2002). "Cutting Edge: Immune Cells as Sources and Targets of the IL-10 Family Members?," *Journal of Immunology* 168(11):5397-5402.

Wolk, K. et al. (May 2006). "IL-22 Regulates the Expression of Genes Responsible for Antimicrobial Defense, Cellular Differentiation, and Mobility in Keratinocytes: A Potential Role in Psoriasis," *Eur J Immunol.* 36:1309-1323.

Wu, C. et al. (Nov. 2007; e-pub. Oct. 14, 2007). "Simultaneous Targeting of Multiple Disease Mediators by a Dual-Variable-Domain Immunoglobulin," *Nat. Biotechnol.* 25(11):1290-1297.

Xie, M.H. et al. (Oct. 6, 2000; e-pub. Jun. 29, 2000). "Interleukin (IL)-22, a novel human cytokine that signals through the interferon receptor-related proteins CRF2-4 and IL-22R," *J. Biol. Chem.* 275(40):31335-31339.

Yang, L. et al. (Aug. 2010; e-published on Apr. 21, 2010). "Amelioration of High Fat Diet Induced Liver Lipogenesis and Hepatic Steatosis by Interleukin-22," *Journal of Hepatology* 53(2):339-347.

Yasuda. (1993). *Biomedicine and Therapeutics* 27(10):1221-1223, (English translation of the Introduction only).

Yelton, M.M. et al. (Mar. 1, 1984). "Transformation of *Aspergillus nidulans* by Using a trpC Plasmid," *Proc. Natl. Acad. Sci. USA* 81(5):1470-1474.

You, M. et al. (Jul. 2004). "Recent Advances in Alcoholic Liver Disease-II. Minireview: Molecular Mechanisms of Alcoholic Fatty Liver," *Am J. Gastrointest Liver Physiol.* 287:GI-G6.

Zamecnik, P.C. et al. (Jun. 1, 1986). "Inhibition of Replication and Expression of Human T-Cell Lymphotropic Virus Type III in Cultured Cells by Exogenous Synthetic Oligonucleotides Complementary to Viral RNA," *Proc. Natl. Acad. Sci. USA* 83)12):4143-4146.

Zenewicz, L.A. et al. (Oct. 2007, e-pub. Oct. 4, 2007). "Interleukin-22 but Not Interleukin-17 Provides Protection to Hepatocytes during Acute Liver Inflammation," *Immunity* 27:647-659.

Zheng, X.X. et al. (1995). "Administration of Noncytolytic IL-10/Fc in Murine Models of Lipopolysaccharide-Induced Septic Shock and Allogeneic Islet Transplantation," *J. Immunol.* 154(10):5590-5600.

Zheng, Y. et al. (Feb. 8, 2007, e-pub. Dec. 24, 2006) "Interleukin-22, a $T_H17$ Cytokine, Mediates IL-23-Induced Dermal Inflammation and Acanthosis," *Nature* 445:647-651.

Zheng, Y. et al. (Mar. 2008, e-pub. Feb. 10, 2008) "Interleukin-22 Mediates Early Host Defense Against Attaching and Effacing Bacterial Pathogens," *Nat Med* 14:282-289.

Zhu, H. et al. (Nov. 12, 2004). "STAT3 Induces Anti-Hepatitis C Viral Activity in Liver Cells," *Biochem. Biophys. Res. Commun.* 324(2):518-528.

Canadian Office Action dated Jun. 28, 2017, for Canadian Application No. 2,809,900, filed on Feb. 28, 2013, four pages.

European Communication pursuant to Rules 161(2) and 162 EPC dated Aug. 22, 2016 for EP Application No. 14860301.2, filed on Nov. 6, 2014, two pages.

European Communication Under Rule 71(3) EPC dated Jul. 19, 2017 for EP Application No. 11821115.0, filed on Aug. 30, 2011, five pages.

European Communication Pursuant to Article 94(3) EPC dated Nov. 28, 2016 for EP Application No. 11821115.0, filed on Aug. 30, 2011, four pages.

European Supplementary Search Report dated Jul. 12, 2017 for EP Application No. 14860301.2 filed, on Jun. 7, 2016, seven pages.

European Supplementary Search Report dated Jun. 30, 2017 for EP Application No. 14860161.0, filed on Jun. 7, 2016, seven pages.

Extended European Search Report dated Mar. 13, 2018, for EP Patent Application No. 17210060.4, filed on Dec. 22, 2017, eight pages.

Extended European Search Report dated Oct. 10, 2014, for EP Patent Application No. 11821115.0, filed on Aug. 30, 2011, five pages.

International Preliminary Examination Report Completed on Sep. 3, 2009 for PCT Application No. PCT/US2008/071859 filed on Aug. 1, 2008, four pages.

International Search Report and Written Opinion dated Jun. 23, 2017 for PCT Application No. PCT/US2017/027806, filed on Apr. 14, 2017, twelve pages.

International Search Report and Written Opinion dated Mar. 27, 2015 for PCT Application No. PCT/US2014/64655, filed on Nov. 7, 2014, sixteen pages.

International Search Report dated Apr. 18, 2013, for PCT Patent Application No. PCT/CN2012/087694, filed on Dec. 27, 2012, four pages.

International Search Report dated Dec. 8, 2011 for PCT Patent Application No. PCT/CN2011/079124, filed on Aug. 30, 2011, four pages.

(56) References Cited

OTHER PUBLICATIONS

International Search Report dated Feb. 10, 2015 for International Application No. PCT/CN2014/090520 filed on Nov. 6, 2014, five pages.
International Search Report dated Jan. 30, 2015 for PCT Application No. PCT/CN2014/090519 filed Nov. 6, 2014, six pages.
Written Opinion of the International Searching Authority dated Apr. 18, 2013 for PCT Patent Application No. PCT/CN2012/087694, filed on Dec. 27, 2012, eleven pages.
Written Opinion of the International Searching Authority dated Dec. 8, 2011 for PCT Patent Application No. PCT/CN2011/079124, filed on Aug. 30, 2011, seven pages.
Written Opinion of the International Searching Authority dated Feb. 10, 2015 for International Application No. PCT/CN2014/090520 filed on Nov. 6, 2014, four pages.
Written Opinion of the International Searching Authority dated Jan. 30, 2015 for PCT Application No. PCT/CN2014/090519 filed Nov. 6, 2014, five pages.
Written Opinion of the International Searching Authority dated Nov. 26, 2008 for PCT Application No. PCT/US2008/071859 filed on Aug. 1, 2008, five pages.
Clinical Research (2006). vol. 83, No. 2, p. 238-242. (Cited in the Japanese Decision of Refusal dated Aug. 29, 2013 for Japanese Patent Application No. 2010-520208), ten pages. English translation of the relevant parts referred by the Examiner in the Decision of Refusal is being provided.
Canadian Notice of Allowance dated May 1, 2018, for Canadian Application No. 2,809,900, filed on Feb. 28, 2013, one page.
European Office Action dated Nov. 5, 2018 for EP Application No. 14860301.2 filed, on Jun. 7, 2016, three pages.
European Communication Pursuant to Article 94(3) EPC dated Jun. 15, 2018 for EP Application No. 14860161.0, filed on Jun. 7, 2016, five pages.
International Preliminary Report on Patentability dated Oct. 25, 2018 for PCT Application No. PCT/US2017/027806 filed on Apr. 14, 2017, seven pages.
Japanese Notice of Reasons for Rejection dated Jul. 24, 2018 for JP Application No. 2016-550931 filed on May 5, 2016, six pages.
U.S. Appl. No. 16/093,583, filed Oct. 12, 2018 by Kolls et al.
Australian Office Action dated May 3, 2019 for AU Application No. 2014346051 filed on May 4, 2016, 4 pages.
Chinese Office Action dated Feb. 11, 2019, for CN Application No. 2014800611889 filed on May 6, 2016, 14 pages. (Machine English Translation of the OA is provided).
European Notice of Allowance dated Feb. 13, 2019 for EP Application No. 14860161.0, filed on Jun. 7, 2016, 5 pages.
Japanese Office Action dated Mar. 12, 2019 for JP Application No. 2016-550931 filed on May 5, 2016, 7 pages.
Australian Notice of Acceptance dated Feb. 18, 2020, for Patent Application No. 2014346051 filed May 4, 2016, three pages.
Cobleigh, M.A. et al. (Jan. 2013). "Protective and Pathological Properties of IL-22 in Liver Disease: Implications for Viral Hepatitis," *Am. J. Pathology* 182(1):21-28.
European Extended Search Report dated Nov. 28, 2019, for Patent Application No. 17783333.2, filed Apr. 14, 2017, seven pages.
European Supplementary Search Report dated Jul. 7, 2017 for EP Application No. 14860998.5, filed Nov. 7, 2014, eight pages.
Herrine, S.K. et al. (Jan. 2018). "Fatty Liver Hepatic Steatosis," Merck Manual, one page only.
International Preliminary Report on Patentability dated Jul. 10, 2014, for International Application No. PCT/CN2012/087694, filed Dec. 27, 2012, 21 pages (with attached English translation of the Written Opinion of the International Searching Authority).
Internatinoal Preliminary Report on Patentability dated Jul. 10, 2007, for International Application No. PCT/US05/28186, filed Aug. 8, 2005, four pages.
International Preliminary Report on Patentability dated Jul. 21, 2011, for International Application No. PCT/US2010/20673, filed Jan. 11, 2010, six pages.
International Preliminary Report on Patentability dated Mar. 14, 2013, for International Applicatino No. PCT/CN2011/079124, filed Aug. 30, 2011, fourteen pages (with attached English translation).
Internatinoal Preliminary Report on Patentability dated May, 10, 2016 for International Application No. PCT/CN/2014/090520, filed Nov. 6, 2014, six pages.
International Preliminary Report on Patentability dated May 10, 2016 for International Application No. PCT/US2014/064655, filed Nov. 7, 2014, eleven pages.
International Preliminary Report on Patentability dated May 19, 2016, for International Application No. PCT/CN2014/090519, filed Nov. 6, 2014, seven pages.
International Search Report dated Mar. 9, 2010, for International Application No. PCT/US10/20673, filed Jan. 11, 2010, three pages.
International Search Report dated May 3, 2006, for International Application No. PCT/US05/28186, filed Aug. 8, 2005, one page.
International Search Report dated Nov. 26, 2008, for International Application No. PCT/US08/71859, filed Aug. 1, 2008, one page.
Written Opinion of the International Searching Authority dated May 3, 2006, for International Application No. PCT/US05/28186, filed Aug. 8, 2005, three pages.
Written Opinion of the International Searching Authority dated Mar. 9, 2010, for International Application No. PCT/US10/20673, filed Jan. 11, 2010, four pages.
Youdim, A. et al. (Jan. 2018). "Metabolic Syndrome," Merck Manual, four pages.
Zenewicz, L.A. et al. (2011). "Recent Advances in Il-22 Biology," *International Immunol.* 23(3):159-163.

* cited by examiner

```
   1 cgaccaggtt ctccttcccc agtcaccagt tgctcgagtt agaattgtct gcaatggccg
  61 ccctgcagaa atctgtgagc tctttcctta tggggaccct ggccaccagc tgcctccttc
 121 tcttggccct cttggtacag ggaggagcag ctgcgcccat cagctcccac tgcaggcttg
 181 acaagtccaa cttccagcag ccctatatca ccaaccgcac cttcatgctg gctaaggagg
 241 ctagcttggc tgataacaac acagacgttc gtctcattgg ggagaaactg ttccacggag
 301 tcagtatgag tgagcgctgc tatctgatga agcaggtgct gaacttcacc cttgaagaag
 361 tgctgttccc tcaatctgat aggttccagc cttatatgca ggaggtggtg cccttcctgg
 421 ccaggctcag caacaggcta agcacatgtc atattgaagg tgatgacctg catatccaga
 481 ggaatgtgca aaagctgaag gacacagtga aaaagcttgg agagagtgga gagatcaaag
 541 caattggaga actggatttg ctgtttatgt ctctgagaaa tgcctgcatt tgaccagagc
 601 aaagctgaaa aatgaataac taaccccctt ccctgctag aaataacaat tagatgcccc
 661 aaagcgattt tttttaacca aaaggaagat gggaagccaa actccatcat gatgggtgga
 721 ttccaaatga accctgcgt tagttacaaa ggaaaccaat gccacttttg tttataagac
 781 cagaaggtag actttctaag catagatatt tattgataac atttcattgt aactggtgtt
 841 ctatacacag aaaacaattt attttttaaa taattgtctt tttccataaa aaagattact
 901 ttccattcct ttagggggaaa aaaccccctaa atagcttcat gtttccataa tcagtacttt
 961 atatttataa atgtatttat tattattata agactgcatt ttatttatat cattttatta
1021 atatggattt atttatagaa acatcattcg atattgctac ttgagtgtaa ggctaatatt
1081 gatatttatg acaataatta tagagctata acatgtttat ttgacctcaa taaacacttg
1141 gatatcc
```

Fig.1

```
   1 cctaaacagg ctctcctctc acttatcaac tgttgacact tgtgcgatct ctgatggctg
  61 tcctgcagaa atctatgagt ttttcccttta tggggacttt ggccgccagc tgcctgcttc
 121 tcattgccct gtgggcccag gaggcaaatg cgctgcccgt caacacccgg tgcaagcttg
 181 aggtgtccaa cttccagcag ccgtacatcg tcaaccgcac ctttatgctg gccaaggagg
 241 ccagccttgc agataacaac acagacgtcc ggctcatcgg ggagaaactg ttccgaggag
 301 tcagtgctaa agatcagtgc tacctgatga agcaggtgct caacttcacc ctggaagacg
 361 ttctgctccc ccagtcagac aggttccagc cctacatgca ggaggtggta cctttcctga
 421 ccaaactcag caatcagctc agctcctgtc acatcagcgg tgacgaccag aacatccaga
 481 agaatgtcag aaggctgaag gagacagtga aaaagcttgg agagagtgga gagatcaagg
 541 cgattgggga actggacctg ctgtttatgt ctctgagaaa tgcttgcgtc tgagcgagaa
 601 gaagctagaa aacgaagaac tgctccttcc tgccttctaa aaagaacaat aagatccctg
 661 aatggacttt tttactaaag gaaagtgaga agctaacgtc catcatcatt agaagatttc
 721 acatgaaacc tggctcagtt gaaaagaaa atagtgtcaa gttgtccatg agaccagagg
 781 tagacttgat aaccacaaag attcattgac aatatttat tgtcactgat gatacaacag
 841 aaaaataatg tactttaaaa aattgtttga aggaggtta cctctcattc ctttagaaaa
 901 aaagcttatg taacttcatt tccatatcca atattttata tatgtaagtt tatttattat
 961 aagtatacat tttatttatg tcagtttatt aatatggatt tatttataga aacattatct
1021 gctattgata tttagtataa ggcaaataat atttatgaca ataactatgg aaacaagata
1081 tcttaggctt taataaacac atggatatca taaaaaaaaa a
```

Fig.2

MAALQKSVSSFLMGTLATSCLL
LLALLVQGGAAPISSHCRLDK
SNFQQPYITNRTFMLAKEASLA
DNNTDVRLIGEKLFHGVSMSER
CYLMKQVLNFTLEEVLFPQSDR
FQPYMQEVVPFLARLSNRLSTC
HIEGDDLHIQRNVQKLKDTVKK
LGESGEIKAIGELDLLFMSLRN
ACI

Fig.3

MAVLQKSMSFSLMGTLAASCLL
LIALWAQEANALPVNTRCKLEV
SNFQQPYIVNRTFMLAKEASLA
DNNTDVRLIGEKLFRGVSAKDQ
CYLMKQVLNFTLEDVLLPQSDR
FQPYMQEVVPFLTKLSNQLSSC
HISGDDQNIQKNVRRLKETVKK
LGESGEKAIGELDLLFMSLRNA
CV

Fig.4

SEQUENCE LISTING

<160> NUMBER OF SEQ ID NOS: 4

<210> SEQ ID NO 1
<211> LENGTH: 1147
<212> TYPE: DNA
<213> ORGANISM: Homo sapiens

<400> SEQUENCE: 1

```
cgaccaggtt ctccttcccc agtcaccagt tgctcgagtt agaattgtct gcaatggccg      60
ccctgcagaa atctgtgagc tctttcctta tggggaccct ggccaccagc tgcctccttc     120
tcttggccct cttggtacag ggaggagcag ctgcgcccat cagctcccac tgcaggcttg     180
acaagtccaa cttccagcag ccctatatca ccaaccgcac cttcatgctg gctaaggagg     240
ctagcttggc tgataacaac acagacgttc gtctcattgg ggagaaactg ttccacggag     300
tcagtatgag tgagcgctgc tatctgatga agcaggtgct gaacttcacc cttgaagaag     360
tgctgttccc tcaatctgat aggttccagc cttatatgca ggaggtggtg cccttcctgg     420
ccaggctcag caacaggcta agcacatgtc atattgaagg tgatgacctg catatccaga     480
ggaatgtgca aaagctgaag gacacagtga aaaagcttgg agagagtgga gagatcaaag     540
caattggaga actggatttg ctgtttatgt ctctgagaaa tgcctgcatt tgaccagagc     600
aaagctgaaa atgaataac taacccccctt tccctgctag aaataacaat tagatgcccc     660
aaagcgattt tttttaacca aaaggaagat gggaagccaa actccatcat gatgggtgga     720
ttccaaatga acccctgcgt tagttacaaa ggaaaccaat gccacttttg tttataagac     780
cagaaggtag actttctaag catagatatt tattgataac atttcattgt aactggtgtt     840
ctatacacag aaaacaattt atttttttaaa taattgtctt tttccataaa aaagattact     900
ttccattcct ttaggggaaa aaacccctaa atagcttcat gtttccataa tcagtacttt     960
atatttataa atgtatttat tattattata agactgcatt ttatttatat cattttatta    1020
atatggattt atttatagaa acatcattcg atattgctac ttgagtgtaa ggctaatatt    1080
gatatttatg acaataatta tagagctata acatgtttat ttgacctcaa taaacacttg    1140
gatatcc                                                              1147
```

<210> SEQ ID NO 2
<211> LENGTH: 1121
<212> TYPE: DNA
<213> ORGANISM: Mus musculus

<400> SEQUENCE: 2

```
cctaaacagg ctctcctctc acttatcaac tgttgacact tgtgcgatct ctgatggctg      60
tcctgcagaa atctatgagt ttttcccttg tggggacttt ggccgccagc tgcctgcttc     120
tcattgccct gtgggcccag gaggcaaatg cgctgcccgt caacacccgg tgcaagcttg     180
aggtgtccaa cttccagcag ccgtacatcg tcaaccgcac ctttatgctg gccaaggagg     240
ccagccttgc agataacaac acagacgtcc ggctcatcgg ggagaaactg ttccgaggag     300
tcagtgctaa agatcagtgc tacctgatga agcaggtgct caacttcacc ctggaagacg     360
ttctgctccc ccagtcagac aggttccagc cctacatgca ggaggtggta cctttcctga     420
ccaaactcag caatcagctc agctcctgtc acatcagcgg tgacgaccag aacatccaga     480
agaatgtcag aaggctgaag gagacagtga aaaagcttgg agagagtgga gagatcaagg     540
cgattgggga actggacctg ctgtttatgt ctctgagaaa tgcttgcgtc tgagcgagaa     600
gaagctagaa aacgaagaac tgctccttcc tgccttctaa aaagaacaat aagatccctg     660
```

-continued

```
aatggacttt tttactaaag gaaagtgaga agctaacgtc catcatcatt agaagatttc      720
acatgaaacc tggctcagtt gaaaagaaa atagtgtcaa gttgtccatg agaccagagg       780
tagacttgat aaccacaaag attcattgac aatatttat tgtcactgat gatacaacag       840
aaaaataatg tactttaaaa aattgtttga aaggaggtta cctctcattc ctttagaaaa      900
aaagcttatg taacttcatt tccatatcca atattttata tatgtaagtt tatttattat     960
aagtatacat tttatttatg tcagtttatt aaatatggatt tatttataga aacattatct   1020
gctattgata tttagtataa ggcaaataat atttatgaca ataactatgg aaacaagata    1080
tcttaggctt taataaacac atggatatca taaaaaaaaa a                         1121
```

<210> SEQ ID NO 3
<211> LENGTH: 179
<212> TYPE: PRT
<213> ORGANISM: Homo sapiens

<400> SEQUENCE: 3

```
Met Ala Ala Leu Gln Lys Ser Val Ser Ser Phe Leu Met Gly Thr Leu
1               5                   10                  15

Ala Thr Ser Cys Leu Leu Leu Ala Leu Leu Val Gln Gly Gly Ala
            20                  25                  30

Ala Ala Pro Ile Ser Ser His Cys Arg Leu Asp Lys Ser Asn Phe Gln
        35                  40                  45

Gln Pro Tyr Ile Thr Asn Arg Thr Phe Met Leu Ala Lys Glu Ala Ser
    50                  55                  60

Leu Ala Asp Asn Asn Thr Asp Val Arg Leu Ile Gly Glu Lys Leu Phe
65                  70                  75                  80

His Gly Val Ser Met Ser Glu Arg Cys Tyr Leu Met Lys Gln Val Leu
                85                  90                  95

Asn Phe Thr Leu Glu Glu Val Leu Phe Pro Gln Ser Asp Arg Phe Gln
            100                 105                 110

Pro Tyr Met Gln Glu Val Val Pro Phe Leu Ala Arg Leu Ser Asn Arg
        115                 120                 125

Leu Ser Thr Cys His Ile Glu Gly Asp Asp Leu His Ile Gln Arg Asn
    130                 135                 140

Val Gln Lys Leu Lys Asp Thr Val Lys Lys Leu Gly Glu Ser Gly Glu
145                 150                 155                 160

Ile Lys Ala Ile Gly Glu Leu Asp Leu Leu Phe Met Ser Leu Arg Asn
                165                 170                 175

Ala Cys Ile
```

<210> SEQ ID NO 4
<211> LENGTH: 178
<212> TYPE: PRT
<213> ORGANISM: Mus musculus

<400> SEQUENCE: 4

```
Met Ala Val Leu Gln Lys Ser Met Ser Phe Ser Leu Met Gly Thr Leu
1               5                   10                  15

Ala Ala Ser Cys Leu Leu Leu Ile Ala Leu Trp Ala Gln Glu Ala Asn
            20                  25                  30

Ala Leu Pro Val Asn Thr Arg Cys Lys Leu Glu Val Ser Asn Phe Gln
        35                  40                  45

Gln Pro Tyr Ile Val Asn Arg Thr Phe Met Leu Ala Lys Glu Ala Ser
    50                  55                  60
```

```
Leu Ala Asp Asn Asn Thr Asp Val Arg Leu Ile Gly Glu Lys Leu Phe
 65              70                  75                  80

Arg Gly Val Ser Ala Lys Asp Gln Cys Tyr Leu Met Lys Gln Val Leu
                 85                  90                  95

Asn Phe Thr Leu Glu Asp Val Leu Leu Pro Gln Ser Asp Arg Phe Gln
            100                 105                 110

Pro Tyr Met Gln Glu Val Val Pro Phe Leu Thr Lys Leu Ser Asn Gln
            115                 120                 125

Leu Ser Ser Cys His Ile Ser Gly Asp Asp Gln Asn Ile Gln Lys Asn
130                     135                 140

Val Arg Arg Leu Lys Glu Thr Val Lys Lys Leu Gly Glu Ser Gly Glu
145                 150                 155                 160

Lys Ala Ile Gly Glu Leu Asp Leu Leu Phe Met Ser Leu Arg Asn Ala
                165                 170                 175

Cys Val
```

USE OF INTERLEUKIN-22 IN THE TREATMENT OF FATTY LIVER DISEASE

CROSS-REFERENCE TO RELATED APPLICATION

This application is a continuation application of U.S. application Ser. No. 14/483,175, filed Sep. 11, 2014, which is a divisional application of U.S. Ser. No. 12/672,274 filed Feb. 5, 2010, which is a US national phase application of PCT International Application No. PCT/US08/71859 filed Aug. 1, 2008, in which the PCT International Application claims benefit of China Application No. 200710044592.7, filed on Aug. 6, 2007, the contents of which are incorporated by reference herein in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 7206220001401SeqList.txt, date recorded: Sep. 1, 2017, size: 7 KB).

FIELD OF INVENTION

This invention relates to the medical use of Interleukin-22 (IL-22). In particular, the present invention relates to use of IL-22 in preparation of pharmaceutical composition for treatment of fatty liver disease (FLD).

BACKGROUND OF INVENTION

Fatty liver is a disease in which excessive amounts of lipids accumulate in the liver cells. Normally lipids account for 3%-4% of the total weight of the liver. If the amount of lipid goes beyond 5%, a fatty liver forms. Lipids may comprise up to 40%-50% of the liver weight in severe fatty liver diseases. Fatty liver mainly comes from the disorder of lipid metabolism of the liver. The main form of lipid in the liver is triglyceride, which is characterized by macrovesicular steatosis. Fatty liver can lead to fibrosis of liver, cirrhosis and hepatocellular carcinoma. In US, around 31% of the adults are indicated to have fatty liver by NMR. About 5.2%-11.4% of the populations in China suffer from fatty liver. Epidemiological studies indicate that, the more a region is being developed, the higher the incidence of fatty liver. The incidence of non-alcoholic fatty liver disease (NAFLD) in diabetic patients is 50%. It is as high as ⅔ in obese patients (BMI>30).

There are two forms of fatty liver diseases (FLD). One is alcoholic fatty liver disease (AFLD), which is caused by excessive alcohol intake (greater than 20 g ethanol per day). The toxic metabolite due to chronic and excessive alcohol metabolism in hepatocytes would result in hepatocytes metabolic dysfunction, leading to fatty liver. Alcohol may change the oxidation-reduction potential of NADH/NAD+, therefore inhibiting the oxidation of fatty acid and tricarboxylicacid cycle. In addition, alcohol can promote the synthesis of fat while inhibit the oxidation of liver fat. It can also inhibit activation of PPAR α (peroxisome proliferators-activated receptor-α, You et al., 2004, Am J. Gastrointest, Liver Physiol. 287:G1-G6). The second type of FLD is NAFLD, including non-alcoholic fatty liver disease and steatohepatitis. Non-alcoholic fatty liver diseases can be subdivided into obesity fatty liver, diabetic fatty liver, over-nutritional or malnutritional fatty liver, fatty liver of pregnancy, drug induced fatty liver, fatty liver of hyperlipemia, fatty liver of middle-aged and elderly, etc. Common complications with fatty liver include cholecystitis, cholelithiasis, obesity, hypertension, diabetes, coronary heart disease and etc.

Clinical diagnosis of fatty liver comprises ultrasonic, CT (computerized tomography), mRI Scan and liver biopsy. The most common indicator of fatty liver is the increase of transaminase, including Alanine transaminase (ALT) and Aspartate transaminase (AST). Meanwhile, level of alkaline phosphatase/γ-glutamyl transferase may also increase. An increase of transaminase is indicative of the decrease of liver metabolism and can act as an indicator of fatty liver.

It is believed that NAFLD can be caused by various direct and indirect factors. For example, it may be induced directly by metabolic syndrome including insulin resistance, lipid metabolism dysfunction and etc. It may also be induced indirectly by medicaments such as glucocorticoid, hormones, Tamoxifen, Methotrexate, Zidovudine, Aminodarone, acetylsalicylic acid (ASA), tetracycline, Didanosine, cocaine, perhexilene, hypervitaminosis A, diltizem; toxin such as, Amanitaphalloides Lepiota, Petrochemicals, phosphate, *Bacillus Cereus* toxin, organic solvent; indirect diseases induced such as, lipodystrophy, dysbetalipoproteinemia, Weber-Christian disease, Wolman's disease, acute fatty liver of pregnancy, Reye's syndrome; idiopathic immunodisease such as, inflammatory bowel disease (IBD), arthritis, lupus erythematosus; viral infection such as HIV, HBV; bacterial infections; or severe weight loss such as, starvation, gastric by pass, intestinal operation.

Available clinical therapeutic strategies include, antioxidant, e.g., vitamin C, vitamin E; compounds in methione metabolism, e.g., betaine; metformin, which can sensitize insulin, other similar medications include: thiazolidinediones (TZD), inhibitors of angiotension II receptor; urodeoxycholic acid, which has the effect of cell protection, anti-apoptosis and regulation of immunity; pentoxifylline, which can act by inhibiting inflammatory factors such as tumor necrosis factor (TNF)-α; other medicaments such as troglitazone, rosiglitazone and pioglitazone. All the therapeutic methods are not satisfactory.

Interleukin-22 (IL-22) is a glycoprotein secreted from T cells, also known as IL-10 related T cell-derived inducible factor (IL-TLF). The expression of IL-22 mRNA was originally identified in T cells upon stimulation with IL-9 and in IL-9 stimulated mast cells in murine, and Concanavilin A (Con A) stimulated spleen cells. The human IL-22 mRNA are mainly expressed in isolated peripheral T cells and are upon stimulation by anti-CD3 or Con A. It is also expressed in activated NK cells. Activated T cells are mainly CD4+ cells, especially CD28 pathway activated Th1 cells.

IL-22 consists of 179 amino acids. Dumoutier et al. reported for the first time the cloning of genes of murine and human IL-22 (Dumoutier, et al., JI, 164:1814-1819, 2000; U.S. Pat. Nos. 6,359,117 and 6,274,710). The use of IL-22 in treating pancreatic disease has been disclosed by Gurney et al. (U.S. Pat. No. 6,551,799).

IL-22 are mainly expressed in activated T cells, (specifically, Th17 cells) lectin-stimulated spleen cells (Duroutier JI 2002), IL-2/IL-12 stimulated NK cells (Wolk, K JI 2002) and LPS-stimulated tissues and organs, including intestine, liver, stomach, kidney, lung, heart, thymus, and spleen, in which the increase of expression of IL-22 can be detected.

IL-22 functions by binding to its receptor IL-22R1 and IL-22R2. IL-22R1 is specific receptor for IL-22, which is mainly expressed in skin, kidney, digestive system (pancreas, intestine, liver, large intestine, and colon) and respiratory system (lung, bronchus). Published researches demonstrated that IL-22 is an immuno-modulator.

It is not observed that IL-22 has any pharmacological effects in treating fatty liver disease.

SUMMARY OF INVENTION

It is therefore an object of the present invention to provide an alternative therapeutic method for fatty liver disease.

Accordingly, the present invention, in one aspect, provides the use of IL-22 in manufacture of a composition for treating fatty liver disease.

In another aspect, the present invention provided a method for the treatment of fatty liver disease in a subject, the method comprising administering a pharmaceutically effective amount of IL-22. In a further aspect, the present invention relates to the use of IL-22 in the manufacture of a medicament for treating fatty liver disease.

In one embodiment, IL-22 of the present invention reduces deposition of triglyceride, thereby reducing steatosis. In another embodiment, IL-22 of the present invention reduces the serum triglyceride level of the subject. In a further embodiment, IL-22 of the present invention decrease transaminases, especially, aspartate aminotransferase (AST or SGOT) and alanine aminotransferase (ALT or SGPT). In another embodiment, IL-22 of the present invention reduces Free Fatty Acid in liver tissue.

In various aspects, IL-22 of the present invention includes but is not limited to mammal IL-22 and recombinant mammal IL-22. In a preferred embodiment, IL-22 is human IL-22.

BRIEF DESCRIPTION OF FIGURES

FIG. 1 shows the sequence of human IL-22 mRNA (SEQ ID NO: 1).

FIG. 2 shows the sequence of murine IL-22 mRNA (SEQ ID NO: 2).

FIG. 3 shows the amino acid sequence of human IL-22 mRNA (SEQ ID NO: 3).

FIG. 4 shows the amino acid sequence of murine IL-22 mRNA (SEQ ID NO: 4).

DETAILED DESCRIPTION OF THE PREFERRED EMBODIMENTS

Figure 5:
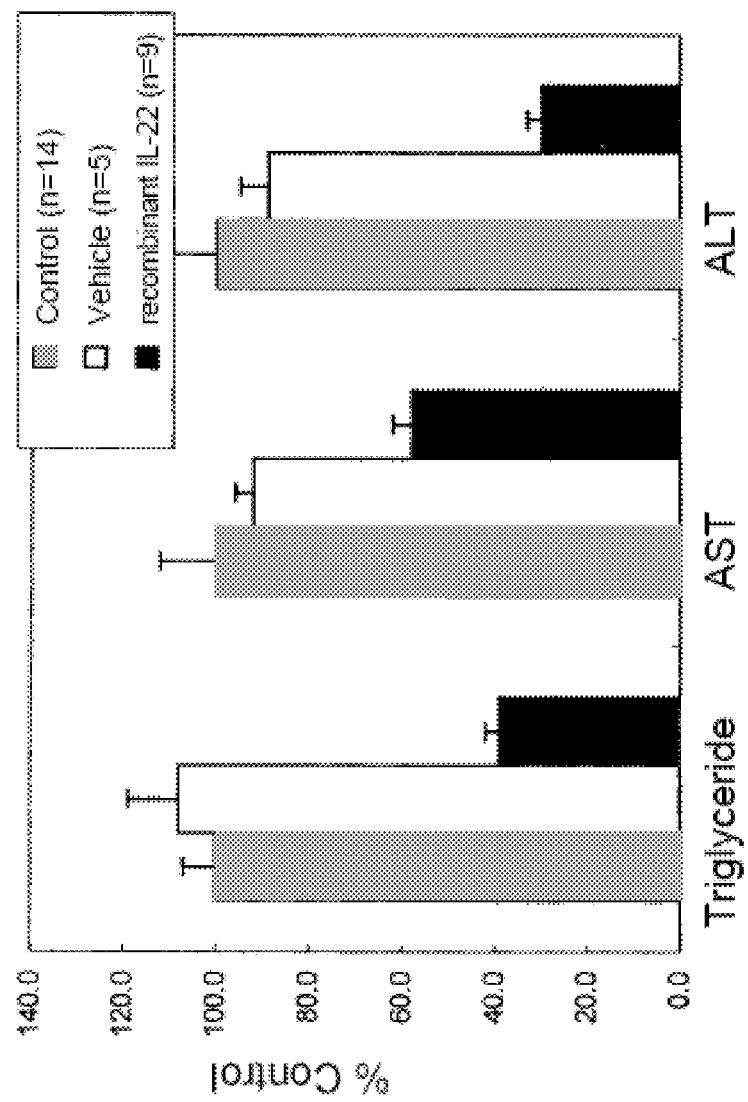
FIG. 5 shows the effect of IL-22 in decreasing levels of serum transaminases in obese ob/ob mice.

It is discovered that, IL-22 is useful in treating either AFLD or NAFLD; it is further discovered that IL-22 is also useful in decreasing levels of serum transaminases.

As used herein and in the claims, "composition" refers to compositions for treating fatty liver or decreasing levels of transaminases.

The term "IL-22" refers to a protein, which has essentially the same amino acid sequence as the human/murine IL-22 as described by Dumoutier in U.S. Pat. No. 6,359,117 and the same biological activity as natural IL-22. IL-22 of the present invention includes but is not limited to human IL-22, recombinant human IL-22, murine IL-22 and recombinant murine IL-22.

The term "has essentially the same amino acid sequence" means having the identical amino acid sequence or having one or more different amino acids residues (with one or more residues missing, addition or replaced), without decreasing the biological activity. In other words, they can still function by binding to IL-22 receptors in target cells. Any such IL-22, either glycosylated (derived from natural or eukaryotic expression system) or un-glycosylated (derived from prokaryotic expression system or chemically synthesized), are within the scope of the present invention.

The term "therapy" refers to administration of IL-22 to a subject in need thereof in order to cure, ameliorate, improve, reduce or impact the disease, symptom, or predisposition of the subject.

The term "subject" refers to mice, human or other mammal animals.

The term "therapeutically effective amount" refers to an amount of IL-22 which can achieve the goal of therapy. It is to be understood by one of ordinary skill in the art that, therapeutically effective dose may change, depending on the routes of administration, the types of other ingredients used and the combination with other medicaments.

IL-22 of the present invention is expressed by recombinant gene clone technique. The expression system includes prokaryotic cells, yeast or higher eukaryotic cells. Suitable prokaryotic cell includes, but is not limited to G$^+$ or G$^-$ bacteria, such as *E. coli*. Available strains of *E. coli* includes K12MM294 (ATCC 31,446), X1776 (ATCC 31,537), W3110 (ATCC 27,325) and K5772 (ATCC 53,635) etc. Other suitable prokaryotic expression system includes, but is not limited to *Erwinia, Klebsiella, Proteus, Salmonella*, such as *Salmonella typhimurium, Serratia* such as *Serratia marcescans, Shigella, B. subtilis, B. licheniformis, Pseudomonas* such as *P. aeruginosa* and *Streptomyces*. *E. coli* W3110 is preferred since it is often used as the host cell for recombinant DNA product.

Besides prokaryotic cells, eukaryotic cells such as filamentous fungi or yeast are also suitable for expression or cloning of IL-22 of the present invention. *Saccharomyces* is a common lower eukaryotic hose microorganism. Other host cells include *Schizosaccharomyces pombe* (Beach and Nurse, Nature, 290:140 [ ]1981; EP 139,383); *Kluyveromyces* hosts (U.S. Pat. No. 4,943,529); Flee et al., Bio Technology, 9:968-975 (1991); such as *K. lactis* (MW98-8C, CBS683, CBS4574; Louvencourt et al., J. Bacteriol., 154

(2):737-742 [1983]), *K. fragilis* (ATCC 12,424), *K. waltii* (ATCC 56,500), *K. drosophilarum* (ATCC 36,906; Van den Berg et al., Bio Technology, 8:135 (1990)), *K. thermotolerans, K. marxianus; yarrowia* (EP 402,226); *Pichia Pastoris* (EP 183,070; Sreekrishna et al., J. Basic Microbiol., 28:265-278 [1988]); *Candida; Trichoderma reesia* (EP 244,234); *Neurospora crassa* (Case et al., Proc. Natl. Acad. Sci. USA, 76:5259-5263 [1979]); *Schwanniomyces* such as *Schwanniomyces occidentalis* (EP 394,538); *Filamentous fungi* such as *Neurospora, Penicillium, Tolypocladium* (WO 91/00357), *Aspergillus* such as *A. nidulans* (Balance et al., Biochem. Biophys. Res. Commum., 112:284-289 [1983]; Tilburm et. al., Gene, 26:205-221 [1983]; Yelton et al., Proc. Natl. Acad. Sci. USA, 81: 1470-1474 [1984]) and *A. niger* (Kelly and Hynes, EMBO J., 4:475-479 [1985]). *Methylotropic yeasts* may also be used to express the IL-22 of the present invention, including but not limited to various types of yeast that can grown in methanol such as *Hansenula, Candida, Kloeckera, Pichia, Saccharomyces, Torulopsis, Rhodotorula*. Typical methylotroph can be found in C. Anthony, The biochemistry of Methylotrophs, 269 (1982).

Host cells used to express glycosylated IL-22 of the present invention are mainly derived from multicellular organism. Examples of invertebrate include insect, such as *Drosophila* S2 and *Spodoptera* Sf9, plant cells. Suitable mammalian cells include Chinese Hamster Ovary (CHO), COS cells, in particular, SV40-transformed CV1 cell line (COS-7, ATCC CRL 1651); human embryo kidney cell line 293 (Graham et al., J. Gen Virol., 36:59 (1997)); CHO/– DHFR (Urlaub and Chasin, Proc. Natl. Acad. Sci. USA, 77:4216 (1980)); murine Sertoli cell (TM4, Mather, Biol. Reprod., 23:243-251) (1980)); human lung cell (W138, ATCC CCL 75); human liver cell (Hep G2, HB 8065); murine breast cancer cells (MMT 060562, ATCC CCL51). One of ordinary skills in the art should be aware how to select suitable host cells.

The above mentioned host cell can be grown on conventional nutrient media after transformed or transfected with IL-22 expression vector or cloning vector. Modified nutrient media is suitable for inducing promoter, selecting transformant or amplifying IL-22 encoding sequence. The selection of nutrient media, temperature and pH is clear to one of ordinary skills in the art. For the general principles for maximizing the proliferation of cultured cells, protocols and techniques, see Mammalian Cell Biotechnology: a Practical Approach, M. Butler, ed. (IRL Press, 1991) and Sambrook et. al., supra.

The method to transfect eukaryotic and transform prokaryotic cells would be clear to one of ordinary skills in the art, such as calcium chloride ($CaCl_2$), calcium phosphate ($CaPO_4$) precipitation, lipofectamine or electroporation. One skilled in the are would be able to select suitable method depending on different host cells. For example, $CaCl_2$ (Sambrook et al., supra.) or electroporation is suitable for eukaryotic cells; *Agrobacterium tumefaciens* is mainly used for the transforming of plant cells (Shaw et. al., Gene, 23:315 (1983) and WO 89/05859); Calcium phosphate precipitation may be used for those mammalian cells without cell walls (Graham and van der Eb, Virology, 52:456-457 (1978)). For a comprehensive description of the method for mammalian cells transfection, see U.S. Pat. No. 4,399,216. For techniques for yeast transfection, see Van Solingen et al., J. Bact., 130:946 (1977) and Hsiao et al., Proc. Natl. Acad. Sci. (USA), 76:3829 (1979). Other techniques for introducing DNA into cells, such as nucleic acid micro-injection, electroporation, bacterial protoplast fusion with intact cells or polycations such as polybrene, polyornithine can be used in the present invention. For various techniques that can be used to transform mammalian cells, see Keown et al., Methods in Enzymology, 185:527-537 (1990) and Mansour et al., Nature, 336:348-352 (1988).

The DNA sequence encoding IL-22 in this invention can be inserted into a replicable vector to clone the gene or express the protein. All the vectors, such as plasmid, cosmid, virion or bacteriophage are publicly available. Applying common techniques in this field, one skilled in the art can insert the DNA sequence encoding IL-22 into appropriate restriction endonuclease sites. A replicable vector usually contains but is not limited to the following parts: one or more signal sequence, one origin of replication, one or more marker gene, one enhancer element, one promoter, and one transcription termination sequence. Applying standard ligation techniques in this field, one skilled in the art can construct an appropriate replicable vector containing one or more above parts.

The IL-22 in this invention can be directly expressed through recombinant DNA, and it can also be produced through fusion of polypeptides. The later can be a signal sequence localized in the mature protein or N-terminal of the polypeptide. It can also be other fragments with specific digesting sites localized in the mature protein or N-terminal of the polypeptide. Usually, the signal sequence is part of the above replicable vector, or part of DNA sequence encoding IL-22 in this invention. The signal sequence can be prokaryotic one, such as Alkaline Phosphatase (ALP), penicillinase, lpp, or the leader sequence of heat-stable enterotoxin. In yeast secretion, the signal sequence can be yeast invertase leader sequence, α factor leader sequence including α factor leader sequence of *Saccharomyces* or *Dekkeromyces*, (see U.S. Pat. No. 5,010,182) or ALP leader sequence, leader sequence of glucose amylase of *C. albicans* (EP 362,179). In mammalian expression system, the mammalian signal sequence can be directly used to secrete the target protein. Such sequence includes signal sequence derived from same or similar species of mammalians and secretion leader sequence of virus.

Both the expression vector and the cloning vector have a piece of DNA sequence, which enables the vector to replicate in one or more corresponding host cells. The sequence corresponding with bacteria, yeast and virus hosts are known to one of ordinary skills in the art. For example, the origin of pBR322 is suitable for most G bacteria, the origin of 2.mu. is suitable for yeast, while the origin of virus (SV40, polymoa virus, adenovirus, VSV or BPV) is suitable for cloning vector in mammalian cells.

Both the expression vector and the cloning vector have a piece of selecting gene, also referred to as "selecting marker". Typical protein expressed by selecting gene (a) is resistant to some antibiotics such as ampicillin, neomycin, methotrexate, tetracyclin and etc, and toxin, (b) is able to remedy auxotrophic deficiencies and (c) supplement some key nutrient factors that complex media can not provide, such as D alanine racemase encoding sequence needed by *bacillus* hosts.

The selecting gene suitable for mammalian host cells shall be able to distinguish the host cells containing IL-22 encoding gene, such as DHFR or thymidine kinase. The proper host cell using wild-type DHFR as selecting gene is CHO strain without DHFR activity. The method of preparation and culture of this strain can be seen in Urlaub et al., Proc. Natl. Acad. Sci. USA, 77:4216 (1980). The selecting gene suitable for yeast cells is trpl gene expressed in yeast plasmid Yrp7 (Stinchcomb et al., nature, 282:39 (1979); Kingsman et al., Gene, 7:141 (1979); Tschemper et al., Gene, 10:157 (1980)). trpl gene can be used to screen yeast mutation strain which can not grow on tryptophan, such as ATCC No. 44047 or PEP4-1 (Jones, Genetics, 85:12 (1977)).

Both expression vector and clone vector usually have a promoter that can be ligated to the IL-22 encoding DNA sequence, which can direct mRNA synthesis. Promoters corresponding to all kinds of hosts are known to one skilled in the art. The promoters suitable for prokaryotic hosts include β-lactamase and lactose promoter system (Chang et al., Nature, 275:615 (1978); Goeddel et al., Nature, 281; 544 (1979)), ALP and trp promoter system (Goeddel, nucleic Acids Res., 8:4057 (1980); EP 36,776), hetero-promoter such as tac promoter (deBoer et al., Proc. Natl. Acad. Sci. USA, 80:21-25 (1983)). Bacterial promoter also has a piece of Shine-Dalgarno (SD) sequence that can be ligated to the IL-22 encoding sequence.

Promoters suitable for yeast host include 3-phosphoglyceric kinase promoter (hitzeman et al., J. Biol. Chem., 255: 2073 (1980)) or other glycolytic enzyme promoters (Hess et al., J. Adv. Enzyme Reg., 7:149 (1968); Holland, Biochemistry, 17:4900 (1978)), such as enolase, glyceraldehydes-3-phosphate dehydrogenase, hexokinase, pyruvate decarboxylase, fructose diphosphatase, glucose-6-phosphate isomerase, triphosphoglycerate mutase, pyruvate kinase, triose phosphate isomerase, glucose phosphate isomerase and glucose kinase.

Some other inducible yeast promoter can regulate transcription according to different growing conditions, including promoters for alcohol dehydrogenase 2, isocytochrome c, acid phosphatase, degrading enzymes related to degradation of nitrogen, Metallothionein, Glyceraldehyde-3-Phosphate, degrading enzymes of maltose and galactose. Detailed description of vectors and promoters suitable for yeast expression system can be seen in EP 73,657.

Promoters can control the transcription of IL-22 encoding gene of the present invention on the replicable vector in mammalian host cells. The promoters include those from certain viral genome such as polymoa virus, Fowlpox Virus, adenovirus, bovine papilloma virus, flow sarcoma virus, cytomegalovirus, retrovirus, HBV, or SV40, from foreign mammalian promoters such as β-actin promoter or immunoglobulin promoter, and those from heat shock protein promoter. However, those promoters should be compatible with the expression system of the host.

The transcription of the IL-22 encoding sequence of the present invention in eukaryotic expression system can be enhanced through the insertion of enhancer into the replicable vectors. Enhancer is a kind of cis-acting element of DNA molecules, usually 10-300 bp, which can enhance the transcription of DNA molecules by acting on the promoters. Numbers of enhancers known enhancers are from mammalian gene, e.g. haptoglobin, elastase, albumin, α-fetoprotein and insulin. The most widely used enhancers are from eukaryotic viral cells, such as SV 40 enhancer (100-270 bp) at the late side of origin, enhancer of cytomegalovirus early promoter, polymoa virus enhancer at the late side of origin, adenovirus enhancer. The enhancers can be inserted into 5' or 3' terminal of the IL-22 encoding sequence on the replicable vectors but 5' terminal is preferred.

The expression vectors in eukaryotic host cells (yeasts, fungi, insects, plants, animals, human, or other nucleated cells from other multicellular organisms) also contain the DNA sequence for terminating transcription and stabilizing mRNA. This kind of sequence is usually derived from the 5' terminal of untranslated region in eukaryotic cells or viral DNA or cDNA, sometimes derived from 3' terminal. The nucleic acid sequences within the untranslated region can be transcripted as acylated polyA sequence at the untranslated region of IL-22 of the present invention.

Other methods, vectors and hosts for synthesizing the IL-22 of the present invention in recombinant vertebrate culture system can be seen in Gething et al., Nature, 293: 620-625 (1981); Mantei et al., Nature, 281:40-46 (1979); EP 117,060 and EP 117,058.

IL-22 can be used as ingredient in a composition for treating fatty liver. The IL-22 includes mammalian IL-22, and/or recombinant mammalian IL-22, or the combinations thereof, preferably, human IL-22, recombinant human IL-22, murine IL-22 and/or recombinant murine IL-22.

The components of the composition in the present invention comprises other ingredients that is useful for treating fatty liver, such as inhibitors and antibodies of inflammatory cytokines, enzymes increasing the metabolism of sugar and lipid, and/or metabolism regulatory protein factors including insulin, glucagon, leptin and adiponectin, etc.

The composition of the present invention may further comprises extracts or compounds that can be used to reduce weight, decrease blood lipid and blood sugar, such as tea extracts, tatins (Simvastatin, Pravastatin, Lovastatin), antioxidants, insulin sensitizers, inhibitors of angiotension converting enzymes and immunoregulatory medications.

The IL-22 of the present invention can be used as a component of composition for decreasing levels of transaminases. The IL-22 includes mammalian IL-22, and/or recombinant mammalian IL-22, or the combinations thereof, preferably, human IL-22, recombinant human IL-22, murine IL-22 and/or recombinant murine IL-22.

The composition in the present invention may further comprise other components that can decrease levels of transaminases.

The IL-22 encoding DNA sequence of the present invention can be used in gene therapy. In the course of gene therapy, a gene is introduced into cells so as to express the product having therapeutic effects in vivo, such as replacing the former defective gene. Gene therapy includes traditional therapy, which has long term effects after one time therapy and administration of gene therapy drugs, in which effective DNA or mRNA are administered one or several times. Antisense RNA or DNA may also be used as gene therapy drugs to block the expression of some genes. It has been demonstrated that antisense oligonucleotide can act as inhibitors in cells, although they are only adsorbed by cell membrane to a limited extent and have a low concentration in cells (Zamecnik et al., Proc. Natl. Acad. Sci. USA 83:4143-4146 [1986]). The absorbance of oligonucleotides may be improved by modification, such as substituent of the negative charged phosphodiester by balance charged groups.

The IL-22 in this invention can be used as medicaments. One skilled in the art can prepare pharmaceutically effective formulation according to common method, which contains effective amount of IL-22 and pharmaceutically acceptable carriers.

When prepared as lyophilization or liquid, physiologically acceptable carrier, excipient, stabilizer need to be added into the pharmaceutical composition in this invention (Remington's Pharmaceutical Sciences $16^{th}$ edition, Osol, A. Ed. (1980)). The dosage and concentration of the carrier, excipient and stabilizer should be safe to the subject (human, mice and other mammals), including buffers such as phosphate, citrate, and other organic acid; antioxidant such as vitamin C; small polypeptide, protein such as serum albumin, gelatin or immunoglobulin; hydrophilic polymer such as PVP, amino acid such as amino acetate, glutamate, asparagine, arginine, lysine; glycose, disaccharide, and other carbohydrate such as glucose, mannose or dextrin; chelate agent such as EDTA; sugar alcohols such as mannitol, sorbitol; counteri ons such as Na$^+$, and/or nonionic surfactant such as as TWEEN™, PLURONICS™ or PEG, et al.

The preparation containing IL-22 in this invention should be sterilized before injection. This procedure can be done using sterile filtration membranes before or after lyophilization and reconstitution.

The pharmaceutical composition is usually filled in a container with sterile access port, such as a i.v. solution bottle with a cork. The cork can be penetrated by hypodermic needle.

The pharmaceutical composition in this invention can be administrated through normal ways, including but not limited to intravenous injection or infusion, intra-abdominal injection, intracephalic injection, intramuscular injection, intraocular injection, intra-arterial injection or infusion, locally or through sustained release systems.

The dosage and concentration can be adjusted according to actual situation. One skilled in the art should know how to choose proper dosage and injection means according to actual situation. The animal experiments in this invention have provided believable instruction for the effective amount in human body. For example, rIL-22 has significant effect in decreasing blood fat at a dose of over 30 µg/kg/d in a dose dependent manner. The principle for adjusting between different species such as mice and human can be seen in Mordenti, J. and Chappell, W. "The use of interspecies scaling in toxicokinetics" In Toxicokinetics and New Drug Development, Yacobi et al.; Pergamon Press, New York 1989, pp. 42-96.

When the IL-22 is injected in mammals, the usual dosage is 1 ng/kg-100 mg/kg body weight per day, preferably 10 µg/kg/d–100 µg/kg/d. The dosage should be adjusted according to different injection means. Direction for certain specific dosage and way of administration can be seen in U.S. Pat. No. 4,657,760; 5,206,344; or 5,225,212. Predictably, different IL-22 formulations would be effective on different diseases. When the target of drugs (organ or tissue) changes, the injection mean shall be adjusted accordingly.

The micro-capsule containing IL-22 of the present invention can be used as sustained release system. Sustained release micro-capsule system of recombinant protein has been successfully applied to rhGH, rhIFN, IL-2 and MNrgp120 (Johnson et al., Nat. Med., 2:795-799 (1996); Yasuda, Biomed. Ther 27:1221-1223 (1993); WO 97/03692, WO 96/40072, WO 96/07399; U.S. Pat. No. 5,654,010).

The sustained release system of IL-22 in this invention can be prepared with PLGA which has good biologically compatibility and degradability. Lactic acid and glycolic acid, the degrading products of PLGA, can be cleared quickly in human body. Furthermore, the degradability of the polymer can vary from several months to several years according to its molecular weight and composition (Lewis, "Controlled release of bioactive agents form lactide/glycolide polymer," in: M. Chasin and R. Langer (Eds.), Biodegradable Polymers as Drug Delivery Systems (Marcel Dekker: New York, 1990), pp. 1-41)).

The IL-22 in this invention can be modified with activated PEG with molecular weight of 5,000-100,000 for the purpose of prolonging its half-life time. Detailed protocols can be seen in Greenwald et al., Bioorg. Med. Chem. Lett. 1994, 4, 2465; Caliceti et al., IL Farmaco, 1993, 48,919; Zalipsky and Lee, Polyethylene Glycol Chemistry: Biotechnical and Biomedical Applications, J. M. Harris, Plenus Press, New York (1992). Multi-arm branched PEG is preferred (CN ZL02101672.0, WO9932139, PCT/US95/0755, PCT/US94/13013, U.S. Pat. Nos. 4,640,835, 4,496,689, 4,301,144, 4,670,417, 4,791,192, 4,179,337).

The IL-22 in this invention can also be prepared as chimeric molecule or fusion protein, for the purpose of enhancing its biological activity or prolonging its half-life time. For example, it can be linked to the whole or partial Fc to express, using whole or partial IL-22 cDNA sequences. The method to produce Fc fusion protein can be seen in U.S. Pat. No. 5,428,130. IL-22 gene can be expressed in the N-terminal or C-terminal of the Fc gene.

Covalently modified IL-22 is also included in this invention. Chemically covalent modification includes modifying N or C terminal or adding a chemical molecule to other amino acid. It also includes modification of amino acid sequence, modification of the glycosylation of IL-22 such as increasing or decreasing glycosylation, or changing of the state of glycosylation directly by chemical reactions (WO87/05330).

Other techniques of formulation as nanotechnology (U.S. 60/544,693), aerosol (CN00114318.2, PCT/CN02/00342), inhalant, et al are also within the scope of this invention.

The technique feature mentioned above or in the examples can be combined randomly. All the features disclosed in the specification can be used in combination with a composition in any form. Each of the features disclosed in the specification can be replaced with any features that have same or similar effect. Therefore unless otherwise stated, the disclosed feature are only exemplary of those same or similar features.

The advantages of the present invention are:
1. IL-22 has the effect of treating fatty liver diseases.
2. IL-22 has the effect of decreasing levels of transaminases (especially, aspartate aminotransferase (AST or SGOT) and alanine aminotransferase (ALT or SGPT).

EXAMPLES

The invention will be further understood by reference to the following examples, which are intended to be purely exemplary of the invention instead of limiting the scope of the invention. For those methods without detailed experimental protocols, one skilled in the art can follow the common methods in the art such as taught by Molecular Clone: a Laboratory Manual, Sambrook et al., New York: Cold Spring Harbor Laboratory Press, 1989, or following the manufacturer's instructions. Unless otherwise stated, all the percentage and ratio are in mass.

Unless otherwise defined, all the terms and expressions used herein have the same meaning as commonly understood by one of ordinary skill in the art. Any methods that are functionally equivalent are within the scope of the invention. The preferred methods and materials are purely exemplary of the invention.

Example 1: Human and Murine IL-22 Gene Cloning

Cloning of human IL-22 gene: Human peripheral blood monocytes were stimulated with anti-human $CD_3$ mAb and cultured for 24 h. Total RNA was extracted by ultracentrifugation, and cDNA was synthesized with the dT primers. Human IL-22 gene was amplified by PCR with the sense primer (5'-GCA GAA TCT TCA GAA CAG GTT C-3') and anti-sense primer (5'-GGC ATC TAA TTG TTA TTT CTA G-3'). The amplified DNA is cloned into E. coli expression vector.

Cloning of mouse IL-22 gene: C57BL/6 female mice were injected with LPS (5 mg/kg, sc). The spleen was obtained after 20 hours. Total RNA was extracted and cDNA was synthesized with the dT primers. Mouse IL-22 gene was amplified by PCR with the sense primer (5'-CTC TCA CTT ATC AAC TGT TGA C-3') and anti-sense primer (5'-GAT GAT GGA CGT TAG CTT CTC AC-3'). The amplified cDNA was cloned into E. coli expression vector pET21(+)

Both human IL-22 and murine IL-22 were verified by DNA sequencing, as shown in FIG. 1 and FIG. 2.

Example 2: Human IL-22 and Mouse IL-22 Gene Expression

E. coli strain BL21(+) was used to express the recombinant protein. The E. coli cells were homogenized under high pressure. IL-22 inclusion bodies were obtained by centrifugation and washed with buffers (Tris-HCl 50 mM, NaCl 100 mM, EDTA 1 mM, DTT 1 mM, and sodium deoxycholate 0.5%) completely. Inclusion bodies were solubilized in 8M urea, 50 mM Mes, 10 mM EDTA, and 0.1 mM DTT, pH 6.5. Inclusion bodies was refolded 4 times for 20 hours in 100 mM Tris-HCl, 2 mM EDTA, 0.5 M L-arginine, 1 mM reduced glutathion, and 0.1 mM oxidized glutathion, pH 8. The mixture was then concentrated and purified using a gel filtration chromatography column sold under the trademark Superdex75™ (Amersham). The protein was eluted with 20 mM Tris-HCl, 50 mM NaCl, pH 7. The purity of IL-22 was determined by SDS-PAGE (>95%) as shown in FIG. 3 and FIG. 4. IL-22 protein aliquot was stored at −80° C.

Example 3: Recombinant IL-22 Decreases Levels of Serum Transaminase in Obese ob/ob Mice The recombinant murine IL-22 obtained in example 2 was injected to obese ob/ob mice (8-12 weeks, 35-50 g) at a dose of 300 µg/kg/d for 14 days. Same amount of vehicle solution (0.1% BSA, PBS) was injected to the mice in control groups. The animals were sacrificed at day 15 and the serum was collected. Levels of serum ALT and AST were determined. The results are shown in FIG. 5.

The results demonstrate that IL-22 can significantly decrease the levels of serum AST and ALT in addition to the decreased levels of serum triglyceride.

Figure 6:
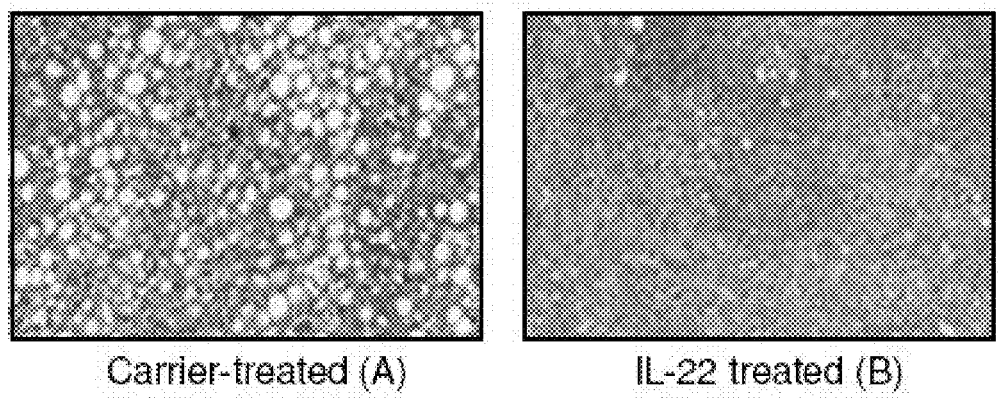
FIG. 6 shows the effect of IL-22 in treating non-alcoholic fatty liver.
  A: Hematoxylin-Eosin stained histologic section of ob/ob mice (control);
  B: Hematoxylin-Eosin stained histologic section of ob/ob mice (IL-22 treatment).

Example 4: Effect of Recombinant IL-22 in Treating Non-Alcoholic Fatty Liver Disease in Obese ob/ob Mice The recombinant murine IL-22 obtained in example 2 was injected to obese ob/ob mice (8-12 weeks, 35-50 g) at a dose of 300 µg/kg/d for 14 days. Same amount of vehicle solution (0.1% BSA, PBS) was injected to the mice in control groups. The animals were sacrificed at day 15. The liver was collected and fixed in 10% formalin. Tissue section was stained with Hematoxylin-Eosin. The results were shown in FIG. 6.

The results demonstrate that the obese ob/ob mice injected with carrier solutions showed obvious steatosis and fatty liver. The obese ob/ob mice injected with IL-22 have a significantly lower degree of steatosis, indicating the effect of IL-22 in treating non-alcoholic fatty liver.

Example 5: Effect of rIL-22 in Treating Alcoholic Fatty Liver in Mice

Figure 7:
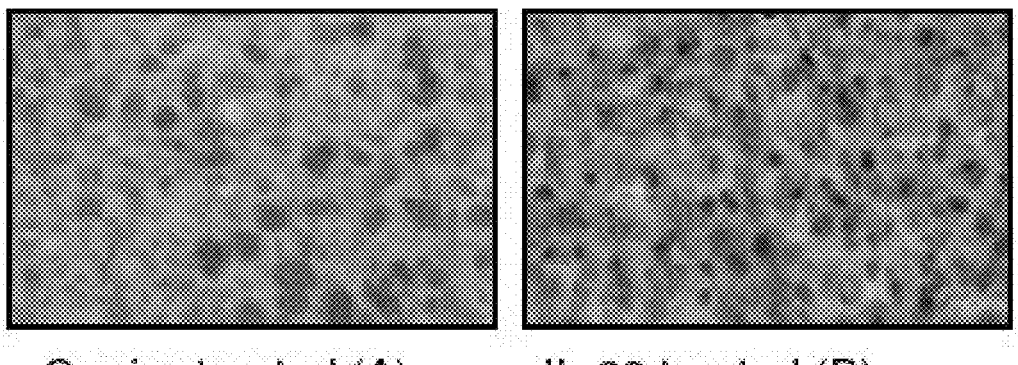
FIG. 7 shows the effect of IL-22 in treating alcohol-induced fatty liver.
  A: Oil Red O stained liver section of ob/ob mice (control);
  B: Oil Red O stained liver section of ob/ob mice (IL-22 treatment)

C57BC/6 mice aged 8-12 weeks were fed with liquid diet containing 20% protein, 10% fat, 45% carbohydrate and 25% alcohol (Lieber et. al., 1989, Hepatology 10:501-510). After 2-3 weeks, the mice were divided into two groups randomly: the control group was injected with same amount of 0.1% BSA, PBS); the treatment group was injected with rIL-22 obtained in example 2 at a dose of 300 µg/kg/d. The animals were sacrificed after 2 weeks. The liver was obtained and assayed. Liver tissue section was stained with Oil Red O. The results were shown in FIG. 7.

The results demonstrate that rIL-22 has significant pharmacological effects in treating alcoholic fatty liver disease by reducing fat content in the liver Example 6: Effects of IL-22 on the Treatment of High Fat Diet-Induced Fatty Liver Disease in Rats The effect of IL-22 in treating high fat diet-induced fatty liver disease was studied in a rat model by establishing fatty liver disease in rats with high fat diet, and treating the animals with rmIL-22 and then analyzing the physiological and histopathological changes in the rats.

Fatty liver disease rat model was established by feeding male SD rats with high-fat diet (with additional 2% cholesterol and 10% lard in the normal diet). The high fat diet contains 8790 kcal/kg, while the normal diet contains 4000 kcal/kg. All experimental animals were fed for high fat diet for 10 weeks. At the end of week 7, rats were randomized and started the treatments with either, control treatment with carrier solution (0.5% BSA PBS), or pegylated rmIL-22 at 30 ug/kg, and 100 ug/kg twice weekly by subcutaneous injection. Body weight was measured weekly. After 3-week treatment, rats were sacrificed. Liver weight, liver triglyceride contents, liver fatty acids, liver histopathological analysis, and serum AST and ALT activity were measured.

Figure 8A:
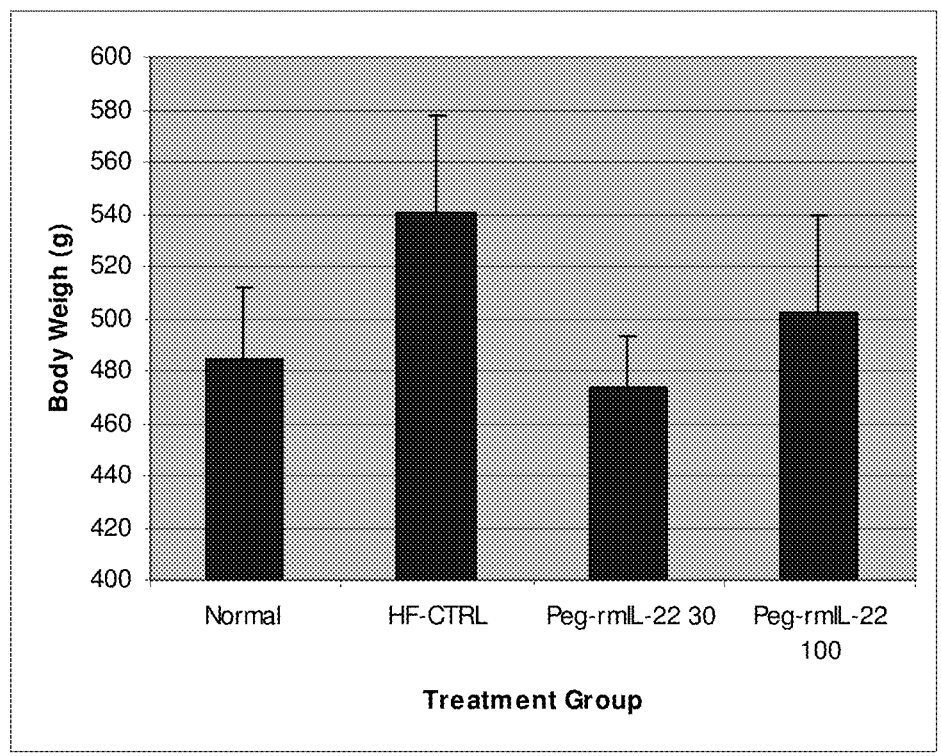
FIG. 8A shows that treatment of high fat diet-induced FLD rats reduced body weight
Figure 8B:
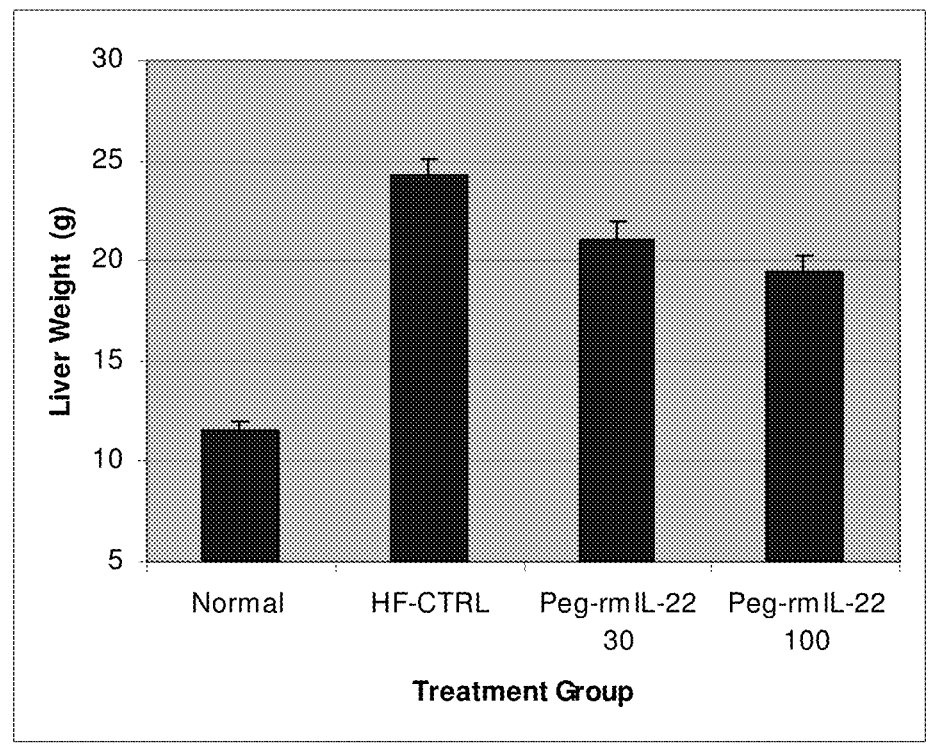
FIG. 8B shows that treatment of high fat diet-induced FLD rats reduced liver weight

Treatment of high-fat diet induced FLD rats with pegylated rmIL-22 demonstrated the following efficacy:

1. Compared to high fat fed control treated rats, treatment of pegylated rmIL-22 (at 30 ug/kg, and 100 ug/kg) significantly reduced the body weight and liver weight (n=5-7), FIG. 8 A/B.

Figure 9A:
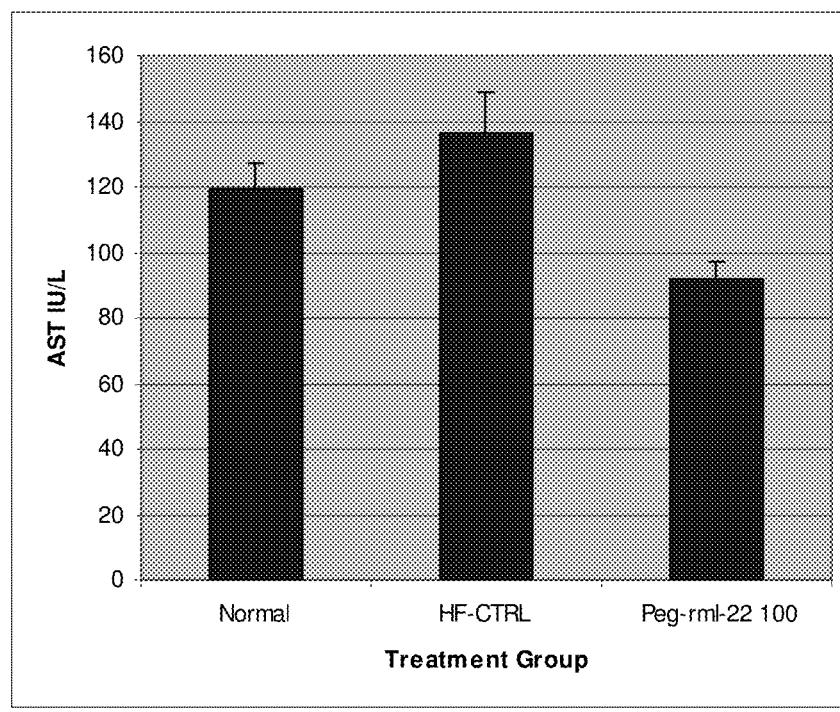
FIG. 9A shows that treatment of high fat diet-induced FLD rats reduced blood AST activities
Figure 9B:
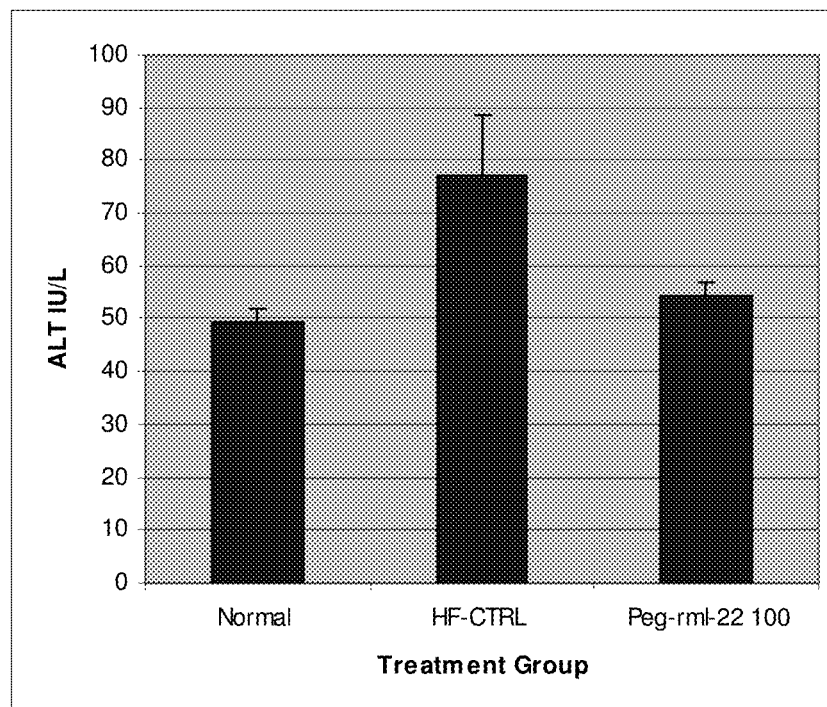
FIG. 9B shows that treatment of high fat diet-induced FLD rats reduced blood ALT activities

2. Compared to the high fat fed control treated rats, treatment of pegylated rmIL-22 (at 100 ug/kg) significantly reduced serum levels of AST and ALT (n=5-7), FIG. 9 A/B.

Figure 10A:
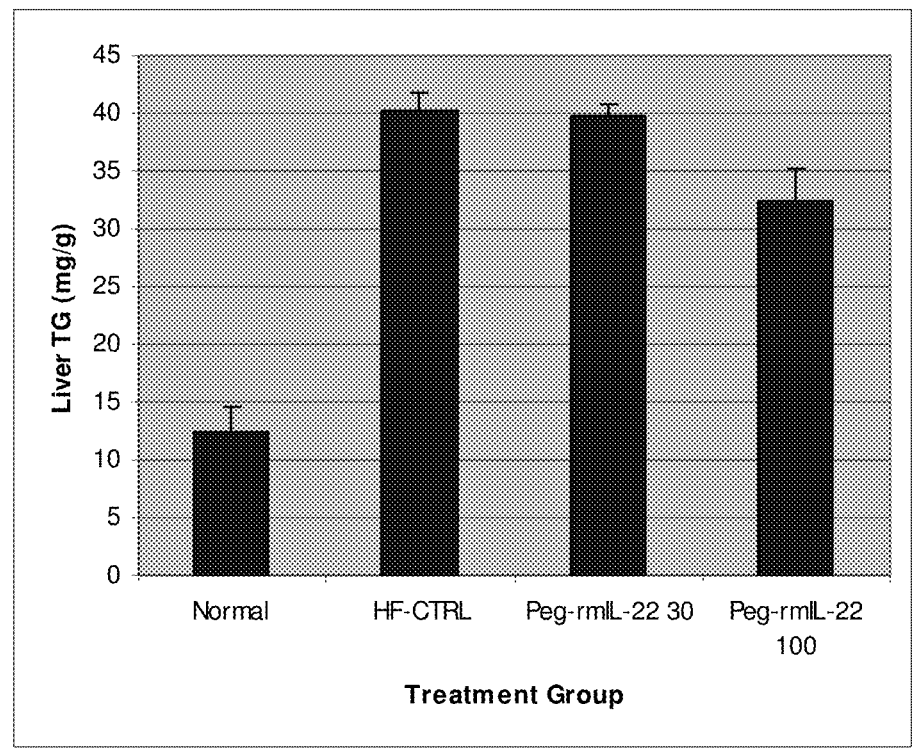
FIG. 10A shows that treatment of high fat diet-induced FLD rats reduced liver triglyceride
Figure 10B:
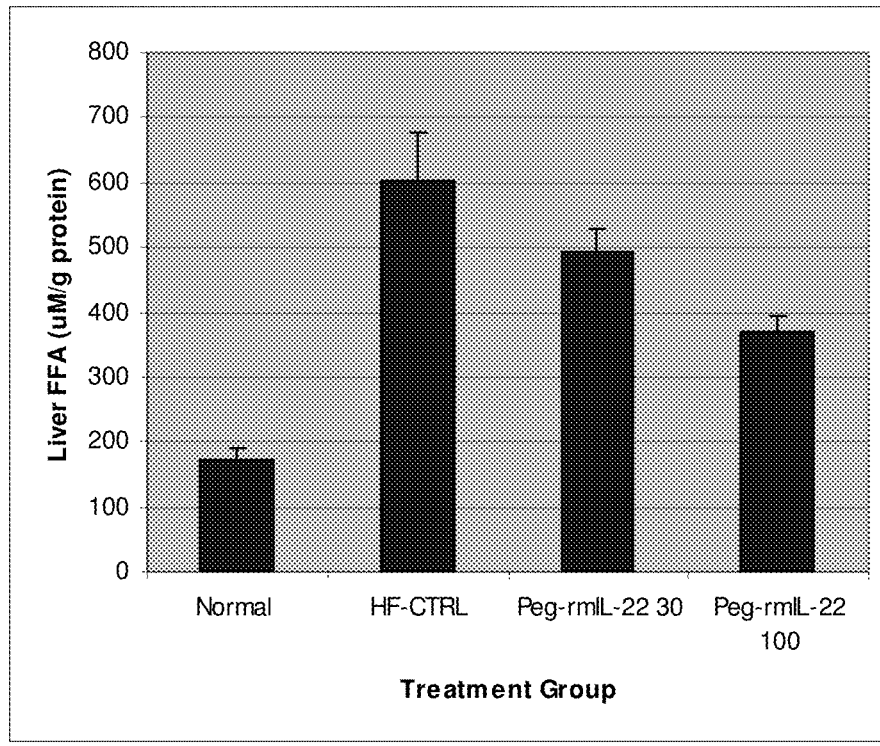
FIG. 10B shows that treatment of high fat diet-induced FLD rats reduced blood free fatty acid contents

3. Compared to control treated group, treatment of pegylated rmIL-22 (at 30 ug/kg and 100 ug/kg) reduced the contents of triglyceride and free fatty acids (FFA) in the liver (n=5-7), FIG. 10 A/B.

Figure 11:
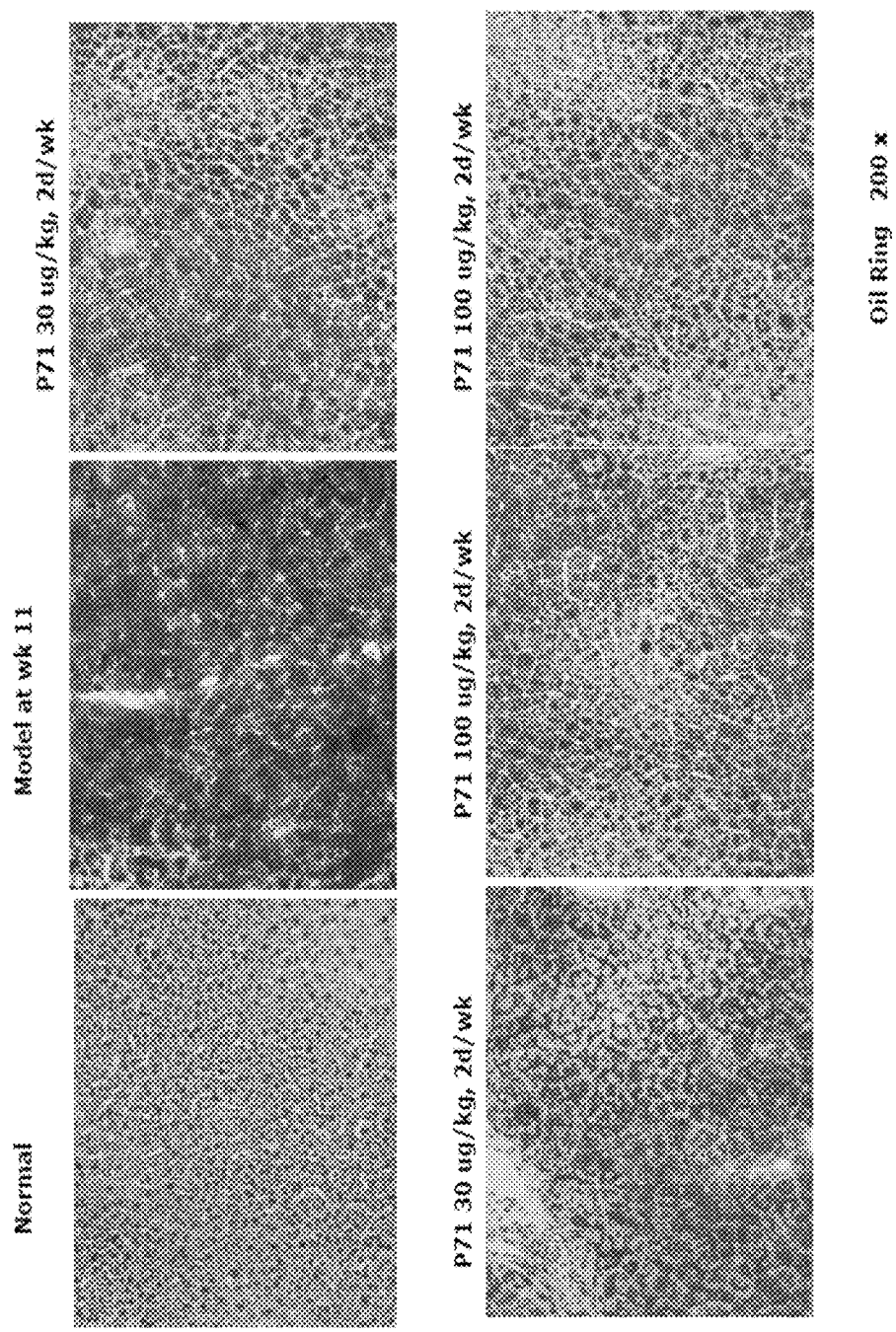
FIG. 11 shows the oil-ring staining of fat in liver.

4. Histopathological analysis of liver sections stained with oil ring staining showed significantly reduced fat deposition in the liver of rats treated with pegylated rmIL-22, FIG. 11.

Figure 12:
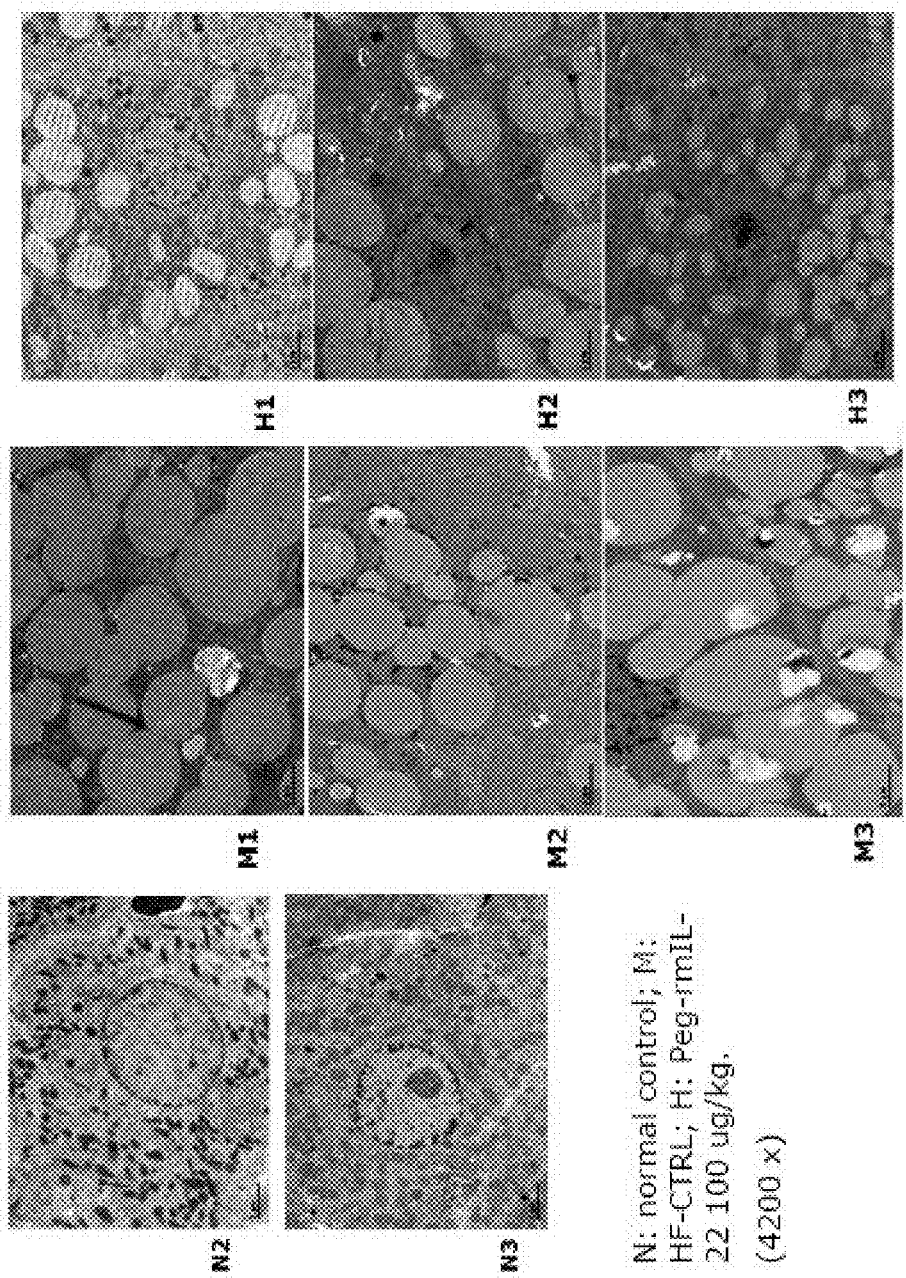
FIG. 12 shows electron microscopy imaging of liver sections showing the size of fat droplets in hepatocytes.

5. Electromicrosopy scanning of hepatocytes demonstrated a significant reduced fat droplets deposition in the liver cells of rats treated with pegylated rmIL-22 (100 ug/kg), FIG. 12.

All the references cited herein are hereby incorporated by reference in their entirety.

Various modifications of the invention, in addition to those shown and described herein, will become apparent to those skilled in the art from the foregoing description. Such modifications are intended to fall within the scope of the appended claims.

What is claimed is:

1. A method for treatment of a subject having fatty liver disease, wherein said method comprises administering to the subject in need of treatment a composition, said composition comprises a pharmaceutically effective amount of IL-22.

2. The method according to claim 1, wherein said IL-22 is human IL-22.

3. The method according to claim 1, wherein said IL-22 is encoded by the polynucleotide of SEQ ID NO: 1.

4. The method according to claim 1, wherein said fatty liver disease is alcoholic fatty liver disease.

5. The method according to claim 1, wherein said composition reduces body weight.

6. The method according to claim 1, wherein said composition reduces liver weight.

7. The method according to claim 1, wherein the pharmaceutically effective amount of IL-22 is 10 μg/kg/d-300 μg/kg/d.

8. The method according to claim 1, wherein the pharmaceutically effective amount of IL-22 is 10 μg/kg/d-100 μg/kg/d.

9. The method according to claim 1, wherein said fatty liver disease is non-alcoholic fatty liver disease.

10. The method according to claim 1, wherein said IL-22 is fused to an Fc.

11. The method according to claim 10, wherein said IL-22 is fused to the N-terminus of the Fc.

12. The method according to claim 10, wherein said IL-22 is fused to the C-terminus of the Fc.

* * * * *